(12) United States Patent
Kimm et al.

(10) Patent No.: US 11,931,509 B2
(45) Date of Patent: *Mar. 19, 2024

(54) SYSTEMS AND METHODS FOR DRIVE PRESSURE SPONTANEOUS VENTILATION

(71) Applicant: Covidien LP, Mansfield, MA (US)

(72) Inventors: Gardner Kimm, Carlsbad, CA (US); Cynthia Miller, Laguna Hills, CA (US); Gary Milne, Louisville, CO (US); Gail Upham, Fallbrook, CA (US); Richard Nakai, Long Beach, CA (US); Peter Doyle, Vista, CA (US); Warren Sanborn, Escondido, CA (US)

(73) Assignee: Covidien LP, Mansfield, MA (US)

( * ) Notice: Subject to any disclaimer, the term of this patent is extended or adjusted under 35 U.S.C. 154(b) by 997 days.

This patent is subject to a terminal disclaimer.

(21) Appl. No.: 16/859,526

(22) Filed: Apr. 27, 2020

(65) Prior Publication Data

US 2020/0254202 A1 Aug. 13, 2020

Related U.S. Application Data

(63) Continuation of application No. 16/174,483, filed on Oct. 30, 2018, now Pat. No. 10,668,239.

(Continued)

(51) Int. Cl.
*A61M 16/00* (2006.01)
*G06F 3/04847* (2022.01)

(52) U.S. Cl.
CPC ...... *A61M 16/024* (2017.08); *A61M 16/0003* (2014.02); *A61M 16/0051* (2013.01);
(Continued)

(58) Field of Classification Search
CPC ... A61B 5/0205; A61B 5/02416; A61B 5/085; A61B 5/087; A61B 5/091; A61B 5/14551; A61B 5/4809; A61B 5/4812; A61B 5/4818; A61B 5/4836; A61B 5/4848; A61B 5/725; A61B 5/7264; A61B 5/7278; A61B 5/7282; A61M 16/00; A61M 16/0003;
(Continued)

(56) References Cited

U.S. PATENT DOCUMENTS 3,669,108 A 6/1972 Sundblom et al.
4,127,123 A 11/1978 Bird
(Continued)

FOREIGN PATENT DOCUMENTS

CN 104135925 A 11/2014
EP 982043 3/2000
(Continued)

OTHER PUBLICATIONS

7200 Series Ventilator, Options, and Accessories: Operator's Manual. Nellcor Puritan Bennett, Part No. 22300 A, Sep. 1990, pp. 1-196.
(Continued)

*Primary Examiner* — Annette Dixon

(57) ABSTRACT

This disclosure describes systems and methods for providing drive pressure ventilation of a patient. The disclosure describes a novel breath type that provides a spontaneous breath type that allows for the calculation of drive pressure that does not require invasive monitoring.

20 Claims, 5 Drawing Sheets

Related U.S. Application Data

(60) Provisional application No. 62/725,490, filed on Aug. 31, 2018, provisional application No. 62/586,077, filed on Nov. 14, 2017.

(52) U.S. Cl.
CPC . *G06F 3/04847* (2013.01); *A61M 2016/0018* (2013.01); *A61M 2016/0027* (2013.01); *A61M 2016/0033* (2013.01); *A61M 2205/18* (2013.01); *A61M 2205/3331* (2013.01); *A61M 2205/3334* (2013.01); *A61M 2205/502* (2013.01); *A61M 2230/42* (2013.01); *A61M 2230/46* (2013.01); *A61M 2230/60* (2013.01)

(58) Field of Classification Search
CPC .......... A61M 16/0009; A61M 16/0051; A61M 16/0057; A61M 16/0063; A61M 16/0066; A61M 16/0069; A61M 16/022; A61M 16/024; A61M 16/026; A61M 16/04; A61M 16/06; A61M 16/0666; A61M 16/0875; A61M 16/204; A61M 16/205; A61M 16/208; A61M 2016/0018; A61M 2016/0021; A61M 2016/0024; A61M 2016/0027; A61M 2016/003; A61M 2016/0033; A61M 2016/0036; A61M 2016/0039; A61M 2016/0042; A61M 2202/0208; A61M 2205/18; A61M 2205/3331; A61M 2205/3334; A61M 2205/502; A61M 2205/505; A61M 2205/52; A61M 2205/581; A61M 2210/1014; A61M 2230/005; A61M 2230/08; A61M 2230/202; A61M 2230/205; A61M 2230/40; A61M 2230/42; A61M 2230/435; A61M 2230/46; A61M 2230/60; A61M 2230/65; G06F 3/04847; G16H 20/40; G16H 50/20
See application file for complete search history.

(56) References Cited

U.S. PATENT DOCUMENTS

| | | | |
|---|---|---|---|
| 4,141,356 A * | 2/1979 | Smargiassi | A61M 16/022 |
| | | | 128/204.26 |
| 4,448,192 A | 5/1984 | Stawitcke et al. | |
| 4,527,557 A | 7/1985 | DeVries et al. | |
| 4,637,385 A | 1/1987 | Rusz | |
| 4,655,213 A | 4/1987 | Rapoport et al. | |
| 4,752,089 A | 6/1988 | Carter | |
| 4,773,411 A | 9/1988 | Downs | |
| 4,805,612 A | 2/1989 | Jensen | |
| 4,805,613 A | 2/1989 | Bird | |
| 4,821,709 A | 4/1989 | Jensen | |
| 4,921,642 A | 5/1990 | LaTorraca | |
| 4,954,799 A | 9/1990 | Kumar | |
| 4,986,268 A | 1/1991 | Tehrani | |
| 5,044,362 A | 9/1991 | Younes | |
| 5,057,822 A | 10/1991 | Hoffman | |
| 5,072,737 A | 12/1991 | Goulding | |
| 5,107,830 A | 4/1992 | Younes | |
| 5,148,802 A | 9/1992 | Sanders et al. | |
| 5,150,291 A | 9/1992 | Cummings et al. | |
| 5,161,525 A | 11/1992 | Kimm et al. | |
| 5,165,398 A | 11/1992 | Bird | |
| 5,237,987 A | 8/1993 | Anderson et al. | |
| 5,239,995 A | 8/1993 | Estes et al. | |
| 5,271,389 A | 12/1993 | Isaza et al. | |
| 5,279,549 A | 1/1994 | Ranford | |
| 5,299,568 A | 4/1994 | Forare et al. | |
| 5,301,921 A | 4/1994 | Kumar | |
| 5,303,698 A | 4/1994 | Tobia et al. | |
| 5,307,795 A | 5/1994 | Whitwam et al. | |
| 5,313,937 A | 5/1994 | Zdrojkowski | |
| 5,319,540 A | 6/1994 | Isaza et al. | |
| 5,325,861 A | 7/1994 | Goulding | |
| 5,333,606 A | 8/1994 | Schneider et al. | |
| 5,339,807 A | 8/1994 | Carter | |
| 5,343,857 A | 9/1994 | Schneider et al. | |
| 5,351,522 A | 10/1994 | Lura | |
| 5,353,788 A | 10/1994 | Miles | |
| 5,357,946 A | 10/1994 | Kee et al. | |
| 5,368,019 A | 11/1994 | LaTorraca | |
| 5,383,449 A | 1/1995 | Forare et al. | |
| 5,385,142 A | 1/1995 | Brady et al. | |
| 5,390,666 A | 2/1995 | Kimm et al. | |
| 5,398,676 A | 3/1995 | Press et al. | |
| 5,401,135 A | 3/1995 | Stoen et al. | |
| 5,402,796 A | 4/1995 | Packer et al. | |
| 5,407,174 A | 4/1995 | Kumar | |
| 5,413,110 A | 5/1995 | Cummings et al. | |
| 5,433,193 A | 7/1995 | Sanders et al. | |
| 5,438,980 A | 8/1995 | Phillips | |
| 5,443,075 A | 8/1995 | Holscher | |
| 5,452,714 A | 9/1995 | Anderson et al. | |
| 5,492,113 A | 2/1996 | Estes et al. | |
| 5,507,282 A | 4/1996 | Younes | |
| 5,513,631 A | 5/1996 | McWilliams | |
| 5,517,983 A | 5/1996 | Deighan et al. | |
| 5,520,071 A | 5/1996 | Jones | |
| 5,524,615 A | 6/1996 | Power | |
| RE35,295 E | 7/1996 | Estes et al. | |
| 5,531,221 A | 7/1996 | Power | |
| 5,535,738 A | 7/1996 | Estes et al. | |
| 5,540,222 A | 7/1996 | Younes | |
| 5,542,415 A | 8/1996 | Brody | |
| 5,544,674 A | 8/1996 | Kelly | |
| 5,549,106 A | 8/1996 | Gruenke et al. | |
| 5,551,418 A | 9/1996 | Estes et al. | |
| 5,572,993 A | 11/1996 | Kurome et al. | |
| 5,582,163 A | 12/1996 | Bonassa | |
| 5,596,984 A | 1/1997 | O'Mahony et al. | |
| 5,598,838 A | 2/1997 | Servidio et al. | |
| 5,630,411 A | 5/1997 | Holscher | |
| 5,632,269 A | 5/1997 | Zdrojkowski | |
| 5,632,270 A | 5/1997 | O'Mahony et al. | |
| 5,645,048 A | 7/1997 | Brodsky et al. | |
| 5,660,171 A | 8/1997 | Kimm et al. | |
| 5,664,560 A | 9/1997 | Merrick et al. | |
| 5,664,562 A | 9/1997 | Bourdon | |
| 5,671,767 A | 9/1997 | Kelly | |
| 5,672,041 A | 9/1997 | Ringdahl et al. | |
| 5,673,689 A | 10/1997 | Power | |
| 5,692,497 A | 12/1997 | Schnitzer et al. | |
| 5,694,923 A | 12/1997 | Hete et al. | |
| 5,704,345 A | 1/1998 | Berthon-Jones | |
| 5,715,812 A | 2/1998 | Deighan et al. | |
| 5,720,278 A | 2/1998 | Lachmann et al. | |
| 5,735,267 A | 4/1998 | Tobia | |
| 5,743,253 A | 4/1998 | Castor et al. | |
| 5,752,506 A | 5/1998 | Richardson | |
| 5,762,480 A | 6/1998 | Adahan | |
| 5,765,558 A | 6/1998 | Psaros et al. | |
| 5,771,884 A | 6/1998 | Yarnall et al. | |
| 5,782,233 A | 7/1998 | Niemi et al. | |
| 5,791,339 A | 8/1998 | Winter | |
| 5,794,615 A | 8/1998 | Estes | |
| 5,794,986 A | 8/1998 | Gansel et al. | |
| 5,803,065 A | 9/1998 | Zdrojkowski et al. | |
| 5,813,399 A | 9/1998 | Isaza et al. | |
| 5,823,187 A | 10/1998 | Estes et al. | |
| 5,826,575 A | 10/1998 | Lall | |
| 5,829,441 A | 11/1998 | Kidd et al. | |
| 5,864,938 A | 2/1999 | Gansel et al. | |
| 5,865,168 A | 2/1999 | Isaza | |
| 5,868,133 A | 2/1999 | DeVries et al. | |
| 5,878,744 A | 3/1999 | Pfeiffer | |
| 5,881,717 A | 3/1999 | Isaza | |
| 5,881,723 A | 3/1999 | Wallace et al. | |
| 5,884,622 A | 3/1999 | Younes | |
| 5,884,623 A | 3/1999 | Winter | |

(56) References Cited

U.S. PATENT DOCUMENTS

| | | |
|---|---|---|
| 5,901,704 A | 5/1999 | Estes et al. |
| 5,904,141 A | 5/1999 | Estes et al. |
| 5,909,731 A | 6/1999 | O'Mahony et al. |
| 5,915,379 A | 6/1999 | Wallace et al. |
| 5,915,380 A | 6/1999 | Wallace et al. |
| 5,915,382 A | 6/1999 | Power |
| 5,918,597 A | 7/1999 | Jones et al. |
| 5,921,238 A | 7/1999 | Bourdon |
| 5,927,274 A | 7/1999 | Servidio et al. |
| 5,934,274 A | 8/1999 | Merrick et al. |
| 5,957,130 A | 9/1999 | Krahbichler et al. |
| 5,970,975 A | 10/1999 | Estes et al. |
| 5,975,081 A | 11/1999 | Hood et al. |
| 6,024,089 A | 2/2000 | Wallace et al. |
| 6,029,664 A | 2/2000 | Zdrojkowski et al. |
| 6,029,665 A | 2/2000 | Berthon-Jones |
| 6,041,777 A | 3/2000 | Faithfull et al. |
| 6,041,780 A | 3/2000 | Richard et al. |
| 6,047,860 A | 4/2000 | Sanders |
| 6,076,523 A | 6/2000 | Jones et al. |
| 6,105,575 A | 8/2000 | Estes et al. |
| 6,116,240 A | 9/2000 | Merrick et al. |
| 6,116,464 A | 9/2000 | Sanders |
| 6,123,073 A | 9/2000 | Schlawin et al. |
| 6,135,105 A | 10/2000 | Lampotang et al. |
| 6,135,106 A | 10/2000 | Dirks et al. |
| 6,142,150 A | 11/2000 | O'Mahony et al. |
| 6,161,539 A | 12/2000 | Winter |
| 6,196,222 B1 | 3/2001 | Heinonen et al. |
| 6,209,540 B1 | 4/2001 | Sugiura et al. |
| 6,213,119 B1 | 4/2001 | Brydon et al. |
| 6,220,245 B1 | 4/2001 | Takabayashi et al. |
| 6,240,919 B1 | 6/2001 | MacDonald et al. |
| 6,253,765 B1 | 7/2001 | Hognelid et al. |
| 6,257,234 B1 | 7/2001 | Sun |
| 6,269,812 B1 | 8/2001 | Wallace et al. |
| 6,273,444 B1 | 8/2001 | Power |
| 6,283,119 B1 | 9/2001 | Bourdon |
| 6,302,105 B1 | 10/2001 | Wickham et al. |
| 6,302,851 B1 | 10/2001 | Gedeon |
| 6,305,372 B1 | 10/2001 | Servidio |
| 6,305,373 B1 | 10/2001 | Wallace et al. |
| 6,305,374 B1 | 10/2001 | Zdrojkowski et al. |
| 6,321,748 B1 | 11/2001 | O'Mahoney |
| 6,325,785 B1 | 12/2001 | Babkes et al. |
| 6,345,619 B1 | 2/2002 | Finn |
| 6,357,438 B1 | 3/2002 | Hansen |
| 6,360,745 B1 | 3/2002 | Wallace et al. |
| 6,369,838 B1 | 4/2002 | Wallace et al. |
| 6,371,113 B1 | 4/2002 | Tobia et al. |
| 6,412,483 B1 | 7/2002 | Jones et al. |
| 6,427,689 B1 | 8/2002 | Estes et al. |
| 6,431,169 B1 | 8/2002 | do Val et al. |
| 6,439,229 B1 | 8/2002 | Du et al. |
| 6,467,477 B1 | 10/2002 | Frank et al. |
| 6,467,478 B1 | 10/2002 | Merrick et al. |
| 6,484,719 B1 | 11/2002 | Berthon-Jones |
| 6,526,970 B2 | 3/2003 | DeVries et al. |
| 6,532,956 B2 | 3/2003 | Hill |
| 6,532,957 B2 | 3/2003 | Berthon-Jones |
| 6,539,940 B2 | 4/2003 | Zdrojkowski et al. |
| 6,546,930 B1 | 4/2003 | Emerson et al. |
| 6,553,991 B1 | 4/2003 | Isaza |
| 6,553,992 B1 | 4/2003 | Berthon-Jones et al. |
| 6,557,553 B1 | 5/2003 | Borrello |
| 6,557,554 B1 | 5/2003 | Sugiura |
| 6,571,795 B2 | 6/2003 | Bourdon |
| 6,575,163 B1 | 6/2003 | Berthon-Jones |
| 6,578,575 B1 | 6/2003 | Jonson |
| 6,581,597 B2 | 6/2003 | Sugiura |
| 6,588,422 B1 | 7/2003 | Berthon-Jones et al. |
| 6,595,213 B2 | 7/2003 | Bennarsten |
| 6,609,517 B1 | 8/2003 | Estes et al. |
| 6,612,995 B2 | 9/2003 | Leonhardt et al. |
| 6,622,726 B1 | 9/2003 | Du |
| 6,626,175 B2 | 9/2003 | Jafari et al. |
| 6,629,527 B1 | 10/2003 | Estes et al. |
| 6,629,934 B2 | 10/2003 | Mault et al. |
| 6,631,716 B1 | 10/2003 | Robinson et al. |
| 6,640,806 B2 | 11/2003 | Yurko |
| 6,644,310 B1 | 11/2003 | Delache et al. |
| 6,651,657 B1 | 11/2003 | Manigel et al. |
| 6,668,824 B1 | 12/2003 | Isaza et al. |
| 6,672,300 B1 | 1/2004 | Grant |
| 6,675,797 B1 | 1/2004 | Berthon-Jones |
| 6,675,801 B2 | 1/2004 | Wallace et al. |
| 6,679,258 B1 | 1/2004 | Strom |
| 6,688,307 B2 | 2/2004 | Berthon-Jones |
| 6,708,691 B1 | 3/2004 | Hayek |
| 6,718,974 B1 | 4/2004 | Moberg |
| 6,725,447 B1 | 4/2004 | Gilman et al. |
| 6,739,337 B2 | 5/2004 | Isaza |
| 6,755,193 B2 | 6/2004 | Berthon-Jones et al. |
| 6,758,217 B1 | 7/2004 | Younes |
| 6,761,167 B1 | 7/2004 | Nadjafizadeh et al. |
| 6,761,168 B1 | 7/2004 | Nadjafizadeh et al. |
| 6,796,305 B1 | 9/2004 | Banner et al. |
| 6,810,876 B2 | 11/2004 | Berthon-Jones |
| 6,814,074 B1 | 11/2004 | Nadjafizadeh et al. |
| 6,820,613 B2 | 11/2004 | Wenkebach |
| 6,823,866 B2 | 11/2004 | Jafari et al. |
| 6,837,242 B2 | 1/2005 | Younes |
| 6,837,244 B2 | 1/2005 | Yagi et al. |
| 6,854,462 B2 | 2/2005 | Berthon-Jones et al. |
| 6,860,858 B2 | 3/2005 | Green et al. |
| 6,866,040 B1 | 3/2005 | Bourdon |
| 6,877,511 B2 | 4/2005 | DeVries et al. |
| 6,899,103 B1 | 5/2005 | Hood et al. |
| 6,910,480 B1 | 6/2005 | Berthon-Jones |
| 6,915,803 B2 | 7/2005 | Berthon-Jones et al. |
| 6,920,878 B2 | 7/2005 | Sinderby et al. |
| 6,932,084 B2 | 8/2005 | Estes et al. |
| 6,948,497 B2 | 9/2005 | Zdrojkowski et al. |
| 6,960,854 B2 | 11/2005 | Nadjafizadeh et al. |
| 6,976,487 B1 | 12/2005 | Melker et al. |
| 6,997,881 B2 | 2/2006 | Green et al. |
| 7,000,610 B2 | 2/2006 | Bennarsten et al. |
| 7,000,612 B2 | 2/2006 | Jafari et al. |
| 7,013,892 B2 | 3/2006 | Estes et al. |
| 7,021,310 B1 | 4/2006 | Sinderby et al. |
| 7,032,589 B2 | 4/2006 | Kerechanin, II et al. |
| 7,036,504 B2 | 5/2006 | Wallace et al. |
| 7,040,321 B2 | 5/2006 | Göbel |
| 7,055,522 B2 | 6/2006 | Berthon-Jones |
| 7,066,173 B2 | 6/2006 | Banner et al. |
| 7,077,131 B2 | 7/2006 | Hansen |
| RE39,225 E | 8/2006 | Isaza et al. |
| 7,096,866 B2 | 8/2006 | Be'eri et al. |
| 7,100,607 B2 | 9/2006 | Zdrojkowski et al. |
| 7,100,609 B2 | 9/2006 | Berthon-Jones et al. |
| 7,117,438 B2 | 10/2006 | Wallace et al. |
| 7,137,389 B2 | 11/2006 | Berthon-Jones |
| 7,152,598 B2 | 12/2006 | Morris et al. |
| 7,162,296 B2 | 1/2007 | Leonhardt et al. |
| 7,210,478 B2 | 5/2007 | Banner et al. |
| 7,225,013 B2 | 5/2007 | Geva et al. |
| 7,246,618 B2 | 7/2007 | Habashi |
| 7,255,103 B2 | 8/2007 | Bassin |
| 7,267,121 B2 | 9/2007 | Ivri |
| 7,270,126 B2 | 9/2007 | Wallace et al. |
| 7,270,128 B2 | 9/2007 | Berthon-Jones et al. |
| 7,296,573 B2 | 11/2007 | Estes et al. |
| 7,305,987 B2 | 12/2007 | Schöller et al. |
| 7,305,988 B2 | 12/2007 | Acker |
| 7,320,320 B2 | 1/2008 | Berthon-Jones |
| 7,334,578 B2 | 2/2008 | Biondi et al. |
| 7,367,337 B2 | 5/2008 | Berthon-Jones et al. |
| 7,369,757 B2 | 5/2008 | Farbarik |
| 7,370,650 B2 | 5/2008 | Nadjafizadeh et al. |
| RE40,402 E | 6/2008 | Leonhardt et al. |
| 7,425,201 B2 | 9/2008 | Euliano |
| 7,428,902 B2 | 9/2008 | Du et al. |
| 7,455,717 B2 | 11/2008 | Sprinkle |
| 7,460,959 B2 | 12/2008 | Jafari |

(56) References Cited

U.S. PATENT DOCUMENTS

| | | | |
|---|---|---|---|
| 7,475,685 B2 | 1/2009 | Dietz et al. |
| 7,484,508 B2 | 2/2009 | Younes |
| 7,487,773 B2 | 2/2009 | Li |
| 7,509,957 B2 | 3/2009 | Duquette et al. |
| 7,516,742 B2 | 4/2009 | Stenzler et al. |
| 7,520,279 B2 | 4/2009 | Berthon-Jones |
| 7,533,670 B1 | 5/2009 | Freitag et al. |
| 7,556,038 B2 | 7/2009 | Kirby et al. |
| 7,588,031 B2 | 9/2009 | Truschel et al. |
| 7,588,543 B2 | 9/2009 | Euliano |
| 7,610,914 B2 | 11/2009 | Bolam et al. |
| 7,617,824 B2 | 11/2009 | Doyle |
| 7,621,270 B2 | 11/2009 | Morris et al. |
| 7,621,271 B2 | 11/2009 | Brugnoli |
| 7,644,713 B2 | 1/2010 | Berthon-Jones |
| 7,654,802 B2 | 2/2010 | Crawford, Jr. et al. |
| 7,672,720 B2 | 3/2010 | Heath |
| 7,678,058 B2 | 3/2010 | Patangay et al. |
| 7,678,061 B2 | 3/2010 | Lee et al. |
| 7,682,312 B2 | 3/2010 | Lurie |
| 7,690,378 B1 | 4/2010 | Turcott |
| 7,694,677 B2 | 4/2010 | Tang |
| 7,697,990 B2 | 4/2010 | Ujhazy et al. |
| 7,708,016 B2 | 5/2010 | Zaiser et al. |
| 7,717,110 B2 | 5/2010 | Kane et al. |
| 7,717,111 B2 | 5/2010 | Schneider et al. |
| 7,717,113 B2 | 5/2010 | Andrieux |
| 7,722,546 B2 | 5/2010 | Madaus et al. |
| D618,356 S | 6/2010 | Ross |
| 7,727,160 B2 | 6/2010 | Green et al. |
| 7,730,886 B2 | 6/2010 | Berthon-Jones |
| 7,751,894 B1 | 7/2010 | Freeberg |
| 7,763,097 B2 | 7/2010 | Federspiel et al. |
| 7,770,578 B2 | 8/2010 | Estes et al. |
| 7,784,461 B2 | 8/2010 | Figueiredo et al. |
| 7,793,659 B2 | 9/2010 | Breen |
| 7,802,571 B2 | 9/2010 | Tehrani |
| 7,810,496 B2 | 10/2010 | Estes et al. |
| 7,810,497 B2 | 10/2010 | Pittman et al. |
| 7,819,815 B2 | 10/2010 | Younes |
| 7,823,588 B2 | 11/2010 | Hansen |
| 7,841,343 B2 | 11/2010 | Deane |
| 7,849,854 B2 | 12/2010 | DeVries et al. |
| 7,855,716 B2 | 12/2010 | McCreary et al. |
| 7,866,318 B2 | 1/2011 | Bassin |
| 7,874,293 B2 | 1/2011 | Gunaratnam et al. |
| D632,796 S | 2/2011 | Ross et al. |
| D632,797 S | 2/2011 | Ross et al. |
| 7,891,354 B2 | 2/2011 | Farbarik |
| 7,893,560 B2 | 2/2011 | Carter |
| 7,914,459 B2 | 3/2011 | Green et al. |
| D638,852 S | 5/2011 | Skidmore et al. |
| 7,934,499 B2 | 5/2011 | Berthon-Jones |
| 7,984,714 B2 | 7/2011 | Hausmann et al. |
| D643,535 S | 8/2011 | Ross et al. |
| 7,992,557 B2 | 8/2011 | Nadjafizadeh et al. |
| 8,001,967 B2 | 8/2011 | Wallace et al. |
| D645,158 S | 9/2011 | Sanchez et al. |
| 8,015,974 B2 | 9/2011 | Christopher |
| 8,021,310 B2 | 9/2011 | Sanborn et al. |
| D649,157 S | 11/2011 | Skidmore et al. |
| D652,521 S | 1/2012 | Ross et al. |
| D652,936 S | 1/2012 | Ross et al. |
| D653,749 S | 2/2012 | Winter et al. |
| 8,113,062 B2 | 2/2012 | Graboi et al. |
| 8,122,885 B2 | 2/2012 | Berthon-Jones |
| D655,405 S | 3/2012 | Winter et al. |
| D655,809 S | 3/2012 | Winter et al. |
| D656,237 S | 3/2012 | Sanchez et al. |
| 8,136,521 B2 | 3/2012 | Matthews |
| 8,181,648 B2 | 5/2012 | Perine et al. |
| 8,210,173 B2 | 7/2012 | Vandine |
| 8,210,174 B2 | 7/2012 | Farbarik |
| 8,240,684 B2 | 8/2012 | Ross et al. |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 8,353,844 B2 | 1/2013 | Jin |
| D692,556 S | 10/2013 | Winter |
| D693,001 S | 11/2013 | Winter |
| 8,603,006 B2 | 12/2013 | Mulqueeny et al. |
| 8,617,083 B2 | 12/2013 | Euliano |
| 8,646,447 B2 | 2/2014 | Martin |
| D701,601 S | 3/2014 | Winter |
| 8,672,858 B2 | 3/2014 | Euliano |
| 8,826,907 B2 | 9/2014 | Masic |
| 8,876,728 B2 | 11/2014 | Baloa Welzien |
| 8,910,632 B2 | 12/2014 | Tiedje |
| 8,920,333 B2 | 12/2014 | Younes |
| 8,950,399 B2 | 2/2015 | Handzsuj |
| 8,960,192 B2 | 2/2015 | Welzien et al. |
| D731,048 S | 6/2015 | Winter |
| D731,049 S | 6/2015 | Winter |
| D731,065 S | 6/2015 | Winter |
| D736,905 S | 8/2015 | Winter |
| 9,155,852 B2 | 10/2015 | Soliman et al. |
| D744,095 S | 11/2015 | Winter |
| 9,220,856 B2 | 12/2015 | Martin |
| 9,392,964 B2 | 7/2016 | Mulqueeny |
| 9,592,356 B2 | 3/2017 | Truschel |
| 9,808,591 B2 | 11/2017 | Esmaeil-zadeh-azar |
| 9,839,760 B2 | 12/2017 | Bonassa |
| 9,895,083 B2 | 2/2018 | Zheng |
| 9,925,346 B2 | 3/2018 | Dong et al. |
| 9,950,129 B2 | 4/2018 | Glenn et al. |
| 9,956,363 B2 | 5/2018 | Masic |
| 9,987,457 B2 | 6/2018 | Winter et al. |
| 10,022,084 B2 | 7/2018 | Nonaka |
| 10,165,966 B2 | 1/2019 | Banner |
| 10,207,068 B2 | 2/2019 | Jafari et al. |
| 10,293,126 B2 | 5/2019 | Berry |
| 10,668,239 B2 * | 6/2020 | Kimm ............... A61M 16/0051 |
| 2005/0034727 A1 | 2/2005 | Shusterman et al. |
| 2005/0039748 A1 | 2/2005 | Andrieux |
| 2005/0139212 A1 | 6/2005 | Bourdon |
| 2006/0155336 A1 | 7/2006 | Heath |
| 2006/0174884 A1 | 8/2006 | Habashi |
| 2006/0235324 A1 | 10/2006 | Lynn |
| 2006/0249148 A1 | 11/2006 | Younes |
| 2006/0278223 A1 * | 12/2006 | Younes ............... A61M 16/026 |
| | | 128/204.23 |
| 2007/0000494 A1 | 1/2007 | Banner et al. |
| 2007/0017515 A1 | 1/2007 | Wallace et al. |
| 2007/0028921 A1 | 2/2007 | Banner et al. |
| 2007/0044796 A1 | 3/2007 | Zdrojkowski et al. |
| 2007/0044799 A1 | 3/2007 | Hete et al. |
| 2007/0077200 A1 | 4/2007 | Baker |
| 2007/0215146 A1 | 9/2007 | Douglas et al. |
| 2007/0227537 A1 | 10/2007 | Bemister et al. |
| 2007/0272241 A1 | 11/2007 | Sanborn et al. |
| 2007/0284361 A1 | 12/2007 | Nadjafizadeh et al. |
| 2008/0011301 A1 | 1/2008 | Qian |
| 2008/0017198 A1 | 1/2008 | Ivri |
| 2008/0045813 A1 | 2/2008 | Phuah et al. |
| 2008/0053441 A1 | 3/2008 | Gottlib et al. |
| 2008/0053443 A1 | 3/2008 | Estes et al. |
| 2008/0053444 A1 | 3/2008 | Estes et al. |
| 2008/0072896 A1 | 3/2008 | Setzer et al. |
| 2008/0072901 A1 | 3/2008 | Habashi |
| 2008/0072902 A1 | 3/2008 | Setzer et al. |
| 2008/0078390 A1 | 4/2008 | Milne et al. |
| 2008/0083644 A1 | 4/2008 | Janbakhsh et al. |
| 2008/0092894 A1 | 4/2008 | Nicolazzi et al. |
| 2008/0097234 A1 | 4/2008 | Nicolazzi et al. |
| 2008/0110461 A1 | 5/2008 | Mulqueeny et al. |
| 2008/0142012 A1 | 6/2008 | Farnsworth et al. |
| 2008/0163872 A1 | 7/2008 | Negele et al. |
| 2008/0185002 A1 | 8/2008 | Berthon-Jones et al. |
| 2008/0196720 A1 | 8/2008 | Kollmeyer et al. |
| 2008/0202528 A1 | 8/2008 | Carter et al. |
| 2008/0216832 A1 | 9/2008 | Carter et al. |
| 2008/0216833 A1 | 9/2008 | Pujol et al. |

(56) References Cited

U.S. PATENT DOCUMENTS

| | | |
|---|---|---|
| 2008/0234595 A1 | 9/2008 | Ranieri et al. |
| 2008/0257349 A1 | 10/2008 | Hedner et al. |
| 2008/0283061 A1 | 11/2008 | Tiedje |
| 2008/0295839 A1 | 12/2008 | Habashi |
| 2009/0020120 A1 | 1/2009 | Schatzl et al. |
| 2009/0020121 A1 | 1/2009 | Bassin |
| 2009/0038616 A1 | 2/2009 | Mulcahy et al. |
| 2009/0056719 A1 | 3/2009 | Newman, Jr. |
| 2009/0084381 A1 | 4/2009 | DeVries et al. |
| 2009/0095298 A1 | 4/2009 | Gunaratnam et al. |
| 2009/0107502 A1 | 4/2009 | Younes |
| 2009/0114224 A1 | 5/2009 | Handzsuj et al. |
| 2009/0159082 A1 | 6/2009 | Eger |
| 2009/0165795 A1 | 7/2009 | Nadjafizadeh et al. |
| 2009/0171176 A1 | 7/2009 | Andersohn |
| 2009/0173347 A1 | 7/2009 | Berthon-Jones |
| 2009/0188502 A1 | 7/2009 | Tiedje |
| 2009/0199855 A1 | 8/2009 | Davenport |
| 2009/0205661 A1 | 8/2009 | Stephenson et al. |
| 2009/0205663 A1 | 8/2009 | Vandine et al. |
| 2009/0221926 A1 | 9/2009 | Younes |
| 2009/0229611 A1 | 9/2009 | Martin et al. |
| 2009/0241951 A1 | 10/2009 | Jafari et al. |
| 2009/0241952 A1 | 10/2009 | Nicolazzi et al. |
| 2009/0241953 A1 | 10/2009 | Vandine et al. |
| 2009/0241955 A1 | 10/2009 | Jafari et al. |
| 2009/0241956 A1 | 10/2009 | Baker, Jr. et al. |
| 2009/0241957 A1 | 10/2009 | Baker, Jr. |
| 2009/0241958 A1 | 10/2009 | Baker, Jr. |
| 2009/0241962 A1 | 10/2009 | Jafari et al. |
| 2009/0247848 A1 | 10/2009 | Baker, Jr. |
| 2009/0247849 A1 | 10/2009 | McCutcheon et al. |
| 2009/0247853 A1 | 10/2009 | Debreczeny |
| 2009/0247891 A1 | 10/2009 | Wood |
| 2009/0287070 A1 | 11/2009 | Baker, Jr. |
| 2009/0301486 A1 | 12/2009 | Masic |
| 2009/0301487 A1 | 12/2009 | Masic |
| 2009/0301490 A1 | 12/2009 | Masic |
| 2009/0301491 A1 | 12/2009 | Masic et al. |
| 2010/0011307 A1 | 1/2010 | Desfossez et al. |
| 2010/0024820 A1 | 2/2010 | Bourdon |
| 2010/0051026 A1 | 3/2010 | Graboi |
| 2010/0051029 A1 | 3/2010 | Jafari et al. |
| 2010/0065055 A1 | 3/2010 | Morris et al. |
| 2010/0065057 A1 | 3/2010 | Berthon-Jones |
| 2010/0069761 A1 | 3/2010 | Karst et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0078017 A1 | 4/2010 | Andrieux et al. |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0137380 A1 | 6/2010 | Maybaum |
| 2010/0137723 A1 | 6/2010 | Patangay et al. |
| 2010/0137729 A1 | 6/2010 | Pierry et al. |
| 2010/0137730 A1 | 6/2010 | Hatlestad |
| 2010/0139660 A1 | 6/2010 | Adahan |
| 2010/0145201 A1 | 6/2010 | Westbrook et al. |
| 2010/0147303 A1 | 6/2010 | Jafari et al. |
| 2010/0152553 A1 | 6/2010 | Ujhazy et al. |
| 2010/0152560 A1 | 6/2010 | Turcott |
| 2010/0170512 A1 | 7/2010 | Kuypers et al. |
| 2010/0174200 A1 | 7/2010 | Wood et al. |
| 2010/0174207 A1 | 7/2010 | Lee et al. |
| 2010/0180898 A1 | 7/2010 | Schneider et al. |
| 2010/0186741 A1 | 7/2010 | Aylsworth et al. |
| 2010/0186742 A1 | 7/2010 | Sherman et al. |
| 2010/0186743 A1 | 7/2010 | Kane et al. |
| 2010/0186744 A1 | 7/2010 | Andrieux |
| 2010/0191076 A1 | 7/2010 | Lewicke et al. |
| 2010/0191137 A1 | 7/2010 | Brada et al. |
| 2010/0192094 A1 | 7/2010 | Jeha et al. |
| 2010/0198086 A1 | 8/2010 | Kuo et al. |
| 2010/0199991 A1 | 8/2010 | Koledin |
| 2010/0210924 A1 | 8/2010 | Parthasarathy et al. |
| 2010/0218764 A1 | 9/2010 | Kwok et al. |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0218773 A1 | 9/2010 | Thornton |
| 2010/0222692 A1 | 9/2010 | McCawley et al. |
| 2010/0224190 A1 | 9/2010 | Tilley et al. |
| 2010/0228133 A1 | 9/2010 | Averina et al. |
| 2010/0228134 A1 | 9/2010 | Martikka et al. |
| 2010/0229863 A1 | 9/2010 | Enk |
| 2010/0234750 A1 | 9/2010 | Ariav et al. |
| 2010/0236553 A1 | 9/2010 | Jafari et al. |
| 2010/0236554 A1 | 9/2010 | Prete |
| 2010/0236555 A1 | 9/2010 | Jafari et al. |
| 2010/0241009 A1 | 9/2010 | Petkie |
| 2010/0242961 A1 | 9/2010 | Mougel et al. |
| 2010/0242965 A1 | 9/2010 | Berthon-Jones |
| 2010/0249549 A1 | 9/2010 | Baker, Jr. et al. |
| 2010/0249630 A1 | 9/2010 | Droitcour et al. |
| 2010/0249631 A1 | 9/2010 | Aoki et al. |
| 2010/0249632 A1 | 9/2010 | Lee et al. |
| 2010/0249633 A1 | 9/2010 | Droitcour et al. |
| 2010/0252037 A1 | 10/2010 | Wondka et al. |
| 2010/0252039 A1 | 10/2010 | Cipollone et al. |
| 2010/0252040 A1 | 10/2010 | Kapust et al. |
| 2010/0252041 A1 | 10/2010 | Kapust et al. |
| 2010/0252042 A1 | 10/2010 | Kapust et al. |
| 2010/0252043 A1 | 10/2010 | Freitag |
| 2010/0256463 A1 | 10/2010 | Greenwald et al. |
| 2010/0258116 A1 | 10/2010 | Federspiel et al. |
| 2010/0258124 A1 | 10/2010 | Madaus et al. |
| 2010/0258126 A1 | 10/2010 | Ujhazy et al. |
| 2010/0258127 A1 | 10/2010 | Hk |
| 2010/0262032 A1 | 10/2010 | Freeberg |
| 2010/0275920 A1 | 11/2010 | Tham et al. |
| 2010/0282259 A1 | 11/2010 | Figueiredo et al. |
| 2010/0288279 A1 | 11/2010 | Seiver et al. |
| 2010/0288283 A1 | 11/2010 | Campbell et al. |
| 2010/0300446 A1 | 12/2010 | Nicolazzi et al. |
| 2010/0307499 A1 | 12/2010 | Eger et al. |
| 2011/0011400 A1 | 1/2011 | Gentner et al. |
| 2011/0017214 A1 | 1/2011 | Tehrani |
| 2011/0023878 A1 | 2/2011 | Thiessen |
| 2011/0023879 A1 | 2/2011 | Vandine et al. |
| 2011/0023880 A1 | 2/2011 | Thiessen |
| 2011/0023881 A1 | 2/2011 | Thiessen |
| 2011/0029910 A1 | 2/2011 | Thiessen |
| 2011/0036352 A1 | 2/2011 | Estes et al. |
| 2011/0041849 A1 | 2/2011 | Chen et al. |
| 2011/0041850 A1 | 2/2011 | Vandine et al. |
| 2011/0126829 A1 | 6/2011 | Carter et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0128008 A1 | 6/2011 | Carter |
| 2011/0132361 A1 | 6/2011 | Sanchez |
| 2011/0132362 A1 | 6/2011 | Sanchez |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0132367 A1 | 6/2011 | Patel |
| 2011/0132368 A1 | 6/2011 | Sanchez et al. |
| 2011/0132369 A1 | 6/2011 | Sanchez |
| 2011/0132371 A1 | 6/2011 | Sanchez et al. |
| 2011/0133936 A1 | 6/2011 | Sanchez et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138315 A1 | 6/2011 | Vandine et al. |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0154241 A1 | 6/2011 | Skidmore et al. |
| 2011/0175728 A1 | 7/2011 | Baker, Jr. |

(56) References Cited

U.S. PATENT DOCUMENTS

| | | |
|---|---|---|
| 2011/0196251 A1 | 8/2011 | Jourdain et al. |
| 2011/0197888 A1 | 8/2011 | Deutsch et al. |
| 2011/0209702 A1 | 9/2011 | Vuong et al. |
| 2011/0209704 A1 | 9/2011 | Jafari et al. |
| 2011/0209707 A1 | 9/2011 | Terhark |
| 2011/0213215 A1 | 9/2011 | Doyle et al. |
| 2011/0230780 A1 | 9/2011 | Sanborn et al. |
| 2011/0249006 A1 | 10/2011 | Wallace et al. |
| 2011/0259330 A1 | 10/2011 | Jafari et al. |
| 2011/0259332 A1 | 10/2011 | Sanchez et al. |
| 2011/0259333 A1 | 10/2011 | Sanchez et al. |
| 2011/0265024 A1 | 10/2011 | Leone et al. |
| 2011/0271960 A1 | 11/2011 | Milne et al. |
| 2011/0273299 A1 | 11/2011 | Milne et al. |
| 2012/0000467 A1 | 1/2012 | Milne et al. |
| 2012/0000468 A1 | 1/2012 | Milne et al. |
| 2012/0000469 A1 | 1/2012 | Milne et al. |
| 2012/0000470 A1 | 1/2012 | Milne et al. |
| 2012/0029317 A1 | 2/2012 | Doyle et al. |
| 2012/0030611 A1 | 2/2012 | Skidmore |
| 2012/0060841 A1 | 3/2012 | Crawford, Jr. et al. |
| 2012/0071729 A1 | 3/2012 | Doyle et al. |
| 2012/0090611 A1 | 4/2012 | Graboi et al. |
| 2012/0096381 A1 | 4/2012 | Milne et al. |
| 2012/0133519 A1 | 5/2012 | Milne et al. |
| 2012/0136222 A1 | 5/2012 | Doyle et al. |
| 2012/0137249 A1 | 5/2012 | Milne et al. |
| 2012/0137250 A1 | 5/2012 | Milne et al. |
| 2012/0157872 A1 | 6/2012 | Welzien et al. |
| 2012/0167885 A1 | 7/2012 | Masic et al. |
| 2012/0185792 A1 | 7/2012 | Kimm et al. |
| 2012/0197578 A1 | 8/2012 | Vig et al. |
| 2012/0197580 A1 | 8/2012 | Vij et al. |
| 2012/0211008 A1 | 8/2012 | Perine et al. |
| 2012/0216809 A1 | 8/2012 | Milne et al. |
| 2012/0216810 A1 | 8/2012 | Jafari et al. |
| 2012/0216811 A1 | 8/2012 | Kimm et al. |
| 2012/0226444 A1 | 9/2012 | Milne et al. |
| 2012/0247471 A1 | 10/2012 | Masic et al. |
| 2012/0272960 A1 | 11/2012 | Milne |
| 2012/0272961 A1 | 11/2012 | Masic et al. |
| 2012/0272962 A1 | 11/2012 | Doyle et al. |
| 2012/0277616 A1 | 11/2012 | Sanborn et al. |
| 2012/0279501 A1 | 11/2012 | Wallace et al. |
| 2012/0304995 A1 | 12/2012 | Kauc |
| 2012/0304997 A1 | 12/2012 | Jafari et al. |
| 2013/0000644 A1 | 1/2013 | Thiessen |
| 2013/0006133 A1 | 1/2013 | Doyle et al. |
| 2013/0006134 A1 | 1/2013 | Doyle et al. |
| 2013/0008443 A1 | 1/2013 | Thiessen |
| 2013/0025596 A1 | 1/2013 | Jafari et al. |
| 2013/0025597 A1 | 1/2013 | Doyle et al. |
| 2013/0032151 A1 | 2/2013 | Adahan |
| 2013/0042869 A1 | 2/2013 | Andrieux et al. |
| 2013/0047983 A1 | 2/2013 | Andrieux et al. |
| 2013/0047989 A1 | 2/2013 | Vandine et al. |
| 2013/0053717 A1 | 2/2013 | Vandine et al. |
| 2013/0074844 A1 | 3/2013 | Kimm et al. |
| 2013/0081536 A1 | 4/2013 | Crawford, Jr. et al. |
| 2013/0104896 A1 | 5/2013 | Kimm et al. |
| 2013/0146055 A1 | 6/2013 | Jafari et al. |
| 2013/0152923 A1 | 6/2013 | Andrieux et al. |
| 2013/0158370 A1 | 6/2013 | Doyle et al. |
| 2013/0159912 A1 | 6/2013 | Baker, Jr. |
| 2013/0167842 A1 | 7/2013 | Jafari et al. |
| 2013/0167843 A1 | 7/2013 | Kimm et al. |
| 2013/0174846 A1 | 7/2013 | Stenqvist |
| 2013/0186397 A1 | 7/2013 | Patel |
| 2013/0186400 A1 | 7/2013 | Jafari et al. |
| 2013/0186401 A1 | 7/2013 | Jafari et al. |
| 2013/0192599 A1 | 8/2013 | Nakai et al. |
| 2013/0220324 A1 | 8/2013 | Jafari et al. |
| 2013/0233314 A1 | 9/2013 | Jafari et al. |
| 2013/0233319 A1 | 9/2013 | Winter et al. |
| 2013/0239038 A1 | 9/2013 | Skidmore et al. |
| 2013/0239967 A1 | 9/2013 | Jafari et al. |
| 2013/0255682 A1 | 10/2013 | Jafari et al. |
| 2013/0255685 A1 | 10/2013 | Jafari et al. |
| 2013/0276788 A1 | 10/2013 | Masic |
| 2013/0283197 A1 | 10/2013 | Skidmore |
| 2013/0284172 A1 | 10/2013 | Doyle et al. |
| 2013/0284173 A1 | 10/2013 | Masic et al. |
| 2013/0284177 A1 | 10/2013 | Li et al. |
| 2013/0327331 A1 | 12/2013 | Bourdon |
| 2013/0333697 A1 | 12/2013 | Carter et al. |
| 2013/0333703 A1 | 12/2013 | Wallace et al. |
| 2013/0338514 A1 | 12/2013 | Karst et al. |
| 2013/0345532 A1 | 12/2013 | Doyle et al. |
| 2014/0000606 A1 | 1/2014 | Doyle et al. |
| 2014/0012150 A1 | 1/2014 | Milne et al. |
| 2014/0034054 A1 | 2/2014 | Angelico et al. |
| 2014/0041656 A1 | 2/2014 | Jourdain et al. |
| 2014/0048071 A1 | 2/2014 | Milne et al. |
| 2014/0048072 A1 | 2/2014 | Angelico et al. |
| 2014/0121553 A1 | 5/2014 | Milne et al. |
| 2014/0123979 A1* | 5/2014 | Doyle ............... G16H 50/20 128/204.23 |
| 2014/0130798 A1 | 5/2014 | Milne et al. |
| 2014/0182590 A1 | 7/2014 | Platt et al. |
| 2014/0224250 A1 | 8/2014 | Sanchez et al. |
| 2014/0251328 A1 | 9/2014 | Graboi et al. |
| 2014/0261409 A1 | 9/2014 | Dong et al. |
| 2014/0261410 A1 | 9/2014 | Sanchez et al. |
| 2014/0261424 A1 | 9/2014 | Doyle et al. |
| 2014/0276176 A1 | 9/2014 | Winter |
| 2014/0290657 A1 | 10/2014 | Vandine et al. |
| 2014/0309507 A1 | 10/2014 | Baker, Jr. |
| 2014/0345616 A1 | 11/2014 | Masic |
| 2014/0360497 A1 | 12/2014 | Jafari et al. |
| 2014/0366879 A1 | 12/2014 | Kimm et al. |
| 2014/0373845 A1 | 12/2014 | Dong |
| 2015/0034082 A1 | 2/2015 | Kimm et al. |
| 2015/0045687 A1 | 2/2015 | Nakai et al. |
| 2015/0090258 A1 | 4/2015 | Milne et al. |
| 2015/0090264 A1 | 4/2015 | Dong |
| 2015/0107584 A1 | 4/2015 | Jafari et al. |
| 2015/0217069 A1 | 8/2015 | Novotni et al. |
| 2015/0231351 A1 | 8/2015 | Jonson |
| 2016/0045694 A1 | 2/2016 | Esmaeil-zadeh-azar |
| 2016/0106938 A1 | 4/2016 | Jourdain et al. |
| 2016/0114115 A1 | 4/2016 | Glenn et al. |
| 2016/0135713 A1 | 5/2016 | Chbat et al. |
| 2016/0243324 A1 | 8/2016 | Doyle et al. |
| 2016/0250427 A1 | 9/2016 | Jafari et al. |
| 2016/0256643 A1 | 9/2016 | Graboi et al. |
| 2016/0256656 A1 | 9/2016 | Glenn et al. |
| 2016/0354566 A1 | 12/2016 | Thiessen |
| 2017/0095627 A1 | 4/2017 | Jafari et al. |
| 2017/0164872 A1 | 6/2017 | Sanborn et al. |
| 2017/0182269 A1 | 6/2017 | Masic et al. |
| 2017/0296765 A1 | 10/2017 | Dong et al. |
| 2018/0036500 A1 | 2/2018 | Esmaeil-zadeh-azar |
| 2018/0193578 A1 | 7/2018 | Glenn et al. |
| 2018/0207378 A1 | 7/2018 | Masic |
| 2018/0207379 A1 | 7/2018 | Masic |
| 2018/0256838 A1 | 9/2018 | Doyle et al. |
| 2019/0143058 A1 | 5/2019 | Kimm |
| 2019/0143059 A1 | 5/2019 | Sanborn |

FOREIGN PATENT DOCUMENTS

| | | |
|---|---|---|
| EP | 1491227 | 12/2004 |
| EP | 858352 | 1/2005 |
| EP | 1515767 | 8/2009 |
| JP | 2000175886 | 6/2000 |
| JP | 2008000436 | 1/2008 |
| JP | 2008178695 | 8/2008 |
| JP | 5608675 | 10/2014 |
| JP | 5858927 | 2/2016 |
| WO | 9014852 | 12/1990 |
| WO | 9214505 | 9/1992 |
| WO | 9308857 | 5/1993 |
| WO | 199715343 | 5/1997 |
| WO | 9812965 | 4/1998 |

(56) References Cited

FOREIGN PATENT DOCUMENTS

| WO | 199951292 | 10/1999 |
|---|---|---|
| WO | 199962580 | 12/1999 |
| WO | 2000/10634 | 3/2000 |
| WO | 200078380 | 12/2000 |
| WO | 01/00264 | 1/2001 |
| WO | 01/00265 | 1/2001 |
| WO | 200174430 | 10/2001 |
| WO | 2002028460 | 4/2002 |
| WO | 2002032488 | 4/2002 |
| WO | 2003008027 | 1/2003 |
| WO | 4047621 | 6/2004 |
| WO | 2005004780 | 1/2005 |
| WO | 2007082384 | 7/2007 |
| WO | 2007102866 | 9/2007 |
| WO | 2007145948 | 12/2007 |
| WO | 2010081223 | 7/2010 |
| WO | 2010121313 | 10/2010 |
| WO | 2011145014 | 11/2011 |
| WO | 2013137797 | 9/2013 |
| WO | 2016189069 | 12/2016 |
| WO | 2017055959 | 4/2017 |

OTHER PUBLICATIONS

7200 Ventilatory System: Addendum/Errata. Nellcor Puritan Bennett, Part No. 4-023576-00, Rev. A, Apr. 1998, pp. 1-32.
800 Operator's and Technical Reference Manual. Series Ventilator System, Nellcor Puritan Bennett, Part No. 4-070088-00, Rev. L, Aug. 2010, pp. 1-476.
840 Operator's and Technical Reference Manual. Ventilator System, Nellcor Puritan Bennett, Part No. 4-075609-00, Rev. G, Oct. 2006, pp. 1-424.
Amato, Marcelo et al., "Driving Pressure and Survival in the Acute Respiratory Distress Syndrome", The NE Journal of Medicine, 372;8, Feb. 19, 2015, 9 pages.
Canadian Office Action in Application 3046571, dated Nov. 6, 2019, 4 pages.
Canadian Office Action in Application 3046571, dated Jul. 24, 2019, 4 pages.
Georgopoulos, Dimitris et al., "Driving Pressure during assisted mechanical ventilation—Is it controlled by patient brain?", Resp Phys & Neur 228 (2016); 69-75.
Grieco, Domenico et al., "Should we use driving pressure to set tidal volume?", Current Opinion, Review, www.co-criticalcare.com, vol. 23, No. 1, Feb. 2017, 7 pages.
Kacmarek, Robert M. et al., "Physiology of Ventilatory Support", Chapter 43, found online at: https://clinicalgate.com/physiology-of-ventilatory-support/, published on Jan. 6, 2015, 19 pgs.
PCT International Search Report and Written Opinion in International Application PCT/US2018/058226, dated Dec. 21, 2018, 19 pages.
Puritan Bennett 980 Series Ventilator Operator's Manual, Covidien, Jan. 29, 2014, Part. No. 10077893 A Jan. 2014, 506 pages.
YouTube Video: "Accurately setting PEEP with transpulmonary pressure", Hamilton Medical, found online at: https://www.youtube.com/watch?v=GH1rtU-1hJc#action=share, 5:09, published on Mar. 2, 2015.
PCT International Preliminary Report on Patentability in International Application PCT/US2018/058226, dated May 19, 2020, 9 pages.
China Office Action dated Jun. 2, 2021 for Chinese Application No. 201880004211.9, 6 pages.

\* cited by examiner

SYSTEMS AND METHODS FOR DRIVE PRESSURE SPONTANEOUS VENTILATION

CROSS-REFERENCE TO RELATED APPLICATIONS

This application is a continuation of U.S. application Ser. No. 16/174,483, filed Oct. 30, 2018, which claims priority to U.S. Provisional Application Ser. No. 62/586,077, filed Nov. 14, 2017, and claims priority to U.S. Provisional Application Ser. No. 62/725,490, filed Aug. 31, 2018, the complete disclosures of which are hereby incorporated herein by reference in their entireties. To the extent appropriate, priority is claimed to each of the above applications.

INTRODUCTION

Medical ventilator systems have long been used to provide ventilatory and supplemental oxygen support to patients. These ventilators typically comprise a source of pressurized gas, such air or oxygen, which is fluidly connected to the patient through a conduit or tubing. As each patient may require a different ventilation strategy, modern ventilators can be customized for the particular needs of an individual patient. For example, several different ventilator modes or settings have been created to provide better ventilation for patients in various different scenarios.

Methods and Systems for Drive Pressure Spontaneous Ventilation

This disclosure describes systems and methods for providing drive pressure ventilation of a patient. The disclosure describes a novel breath type that provides spontaneous ventilation that allows for the calculation of drive pressure that does not require invasive monitoring. To accomplish this goal, the drive pressure (DP) breath type (also referred to herein as drive pressure ventilation) briefly interrupts and smoothly transitions from a base spontaneous breath subtype, into a temporary breath subtype in response to the detection of a condition. As such, ventilator systems and methods utilizing the DP breath type as disclosed herein may adjust ventilator parameters and/or perform other actions based on a monitored dynamic drive pressure.

In part, this disclosure describes a method for drive pressure ventilation of a patient with a ventilator. The method includes ventilating the patient with the ventilator in a spontaneous breath subtype; non-invasively monitoring respiratory data of the patient with at least one of a pressure sensor and a flow sensor operatively coupled to at least one of a patient circuit or a pressure generating system; analyzing the respiratory data to detect a patient effort; delivering inspiratory gas to the patient with the ventilator in response to a detected patient effort; determining an occurrence of a condition by the ventilator based on information gathered by the ventilator, in response to the condition, determining a percent support setting for the PA breath subtype based on a target setting or the respiratory data from the spontaneous breath subtype; automatically and temporarily switching from the spontaneous breath subtype into the PA breath subtype for at least three breaths in response to calculating the percent support setting; estimating a respiratory system compliance and a respiratory system resistance of the patient during the PA breath subtype based on the respiratory data; returning to the spontaneous breath subtype after the at least three breaths; calculating a drive pressure of the patient during the spontaneous breath subtype utilizing the respiratory system compliance, the a respiratory system resistance, and the respiratory data received after the return; and displaying the drive pressure. The spontaneous breath subtype does not include a proportional assist (PA) breath subtype.

Yet another aspect of this disclosure describes a ventilator system for delivering drive pressure ventilation to a patient. The ventilator system includes a pressure generating system, a ventilation tubing system, one or more non-invasive sensors, a controller, and a display. The pressure generating system generates a flow of breathing gas. The ventilation tubing system includes a patient interface. The patient interface connects the pressure generating system to the patient. The one or more non-invasive sensors are operatively coupled to at least one of the pressure generating system or the ventilation tubing system. The one or more non-invasive sensors generate output indicative of at least one of flow, volume or pressure. The controller collects and analyzes the output to determine a condition. In response to the condition, the controller temporarily switches the ventilator system from a spontaneous breath subtype into a proportional assist (PA) breath subtype for at least one breath. The controller estimates a respiratory system compliance of the patient during the PA breath subtype based on the output collected during the PA breath subtype. Additionally, after the at least one breath, the controller switches the ventilator system from the PA breath subtype back to the spontaneous breath subtype. After a return to the spontaneous breath subtype, the controller calculates a drive pressure of the patient based on the respiratory system compliance and the output after the return. The display displays the drive pressure.

The disclosure further describes a non-transitory computer-readable medium having computer-executable instructions for performing a method of ventilating a patient with a ventilator. The method includes ventilating the patient with the ventilator in a spontaneous breath subtype; monitoring respiratory data of the patient with at least one of a pressure sensor and a flow sensor operatively coupled to at least one of a patient circuit or a pressure generating system; analyzing the respiratory data to detect a patient effort; delivering inspiratory gas to the patient with the ventilator in response to a detected patient effort; determining an occurrence of a condition by the ventilator based on information gathered by the ventilator; in response to the condition, automatically and temporarily switching from the spontaneous breath subtype into the PA breath subtype for at least three breaths; estimating a respiratory system compliance and a respiratory system resistance of the patient during the PA breath subtype based on the respiratory data; calculating a drive pressure of the patient during the spontaneous breath subtype utilizing respiratory system compliance, the respiratory system resistance, and the respiratory data received during the spontaneous breath subtype; and performing an action based on the drive pressure. The spontaneous breath subtype does not include a PA breath subtype. A percent support setting for the PA breath subtype is determined based on at least one of a target setting, a non-invasively monitored flow, a non-invasively monitored pressure, or a noninvasively monitor tidal volume during the spontaneous breath subtype from at least one of the pressure sensor and the flow sensor by the ventilator.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The following drawing figures, which form a part of this application, are illustrative of embodiments of systems and methods described below and are not meant to limit the scope of the invention in any manner, which scope shall be based on the claims appended hereto.

DETAILED DESCRIPTION

Figure 1:
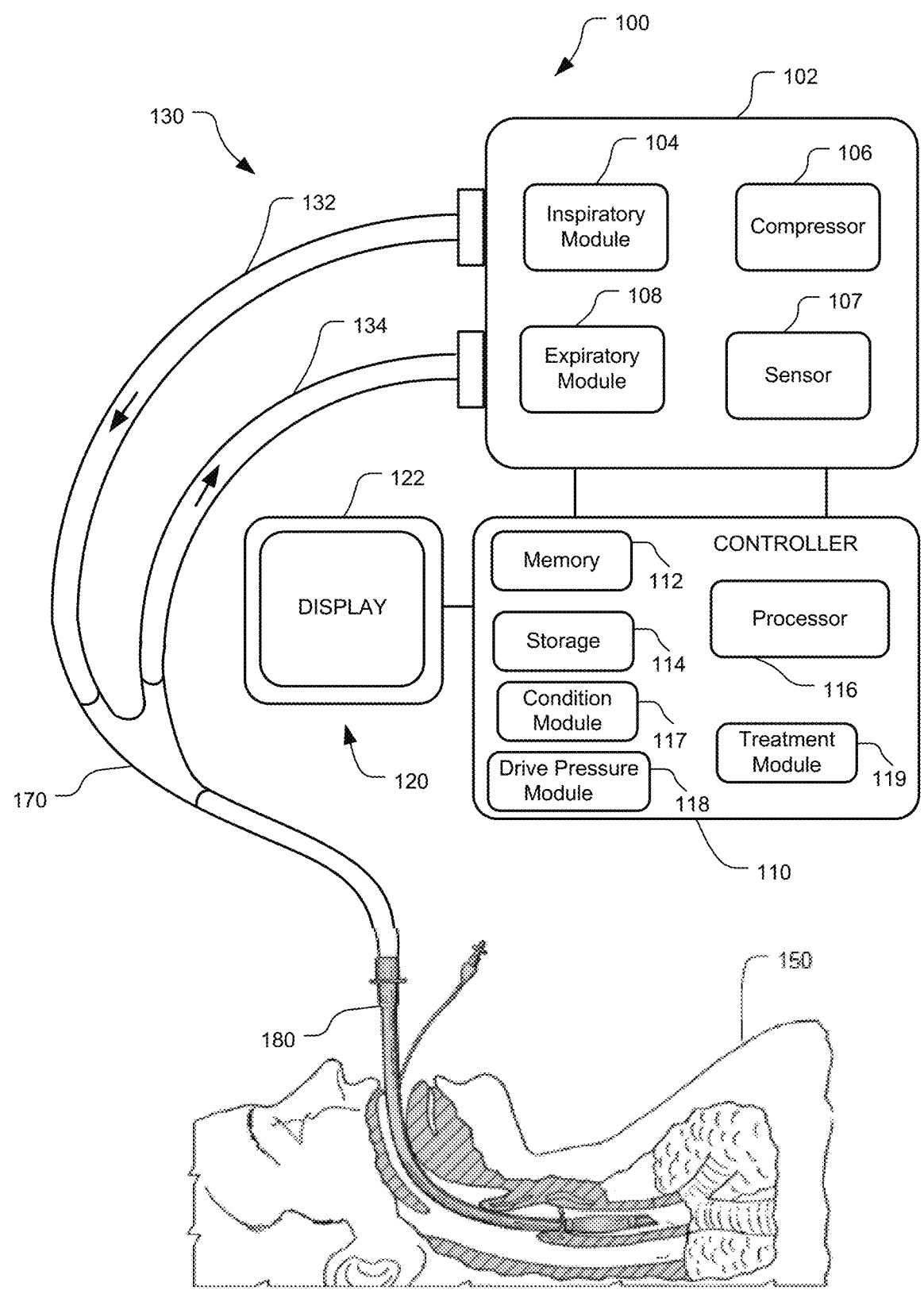
FIG. 1 is a schematic diagram illustrating an example of a ventilator in accordance with aspects of the disclosure.

Although the techniques introduced above and discussed in detail below may be implemented for a variety of medical devices, the present disclosure will discuss the implementation of these techniques in the context of a medical ventilator for use in providing ventilation support to a human patient. A person of skill in the art will understand that the technology described in the context of a medical ventilator for human patients could be adapted for use with other systems such as ventilators for non-human patients and general gas transport systems.

Medical ventilators are used to provide a breathing gas to a patient who may otherwise be unable to breathe sufficiently. In modern medical facilities, pressurized air and oxygen sources are often available from wall outlets. Accordingly, ventilators may provide pressure regulating valves (or regulators) connected to centralized sources of pressurized air and pressurized oxygen. The regulating valves function to regulate flow so that respiratory gas having a desired concentration of oxygen is supplied to the patient at desired pressures and rates. Ventilators capable of operating independently of external sources of pressurized air are also available.

While operating a ventilator, it is desirable to control the percentage of oxygen in the gas supplied by the ventilator to the patient. Further, as each patient may require a different ventilation strategy, modern ventilators can be customized for the particular needs of an individual patient.

For the purposes of this disclosure, a "breath" refers to a single cycle of inspiration and exhalation delivered with the assistance of a ventilator. The term "breath type" refers to some specific definition or set of rules dictating how the pressure and flow of respiratory gas is controlled by the ventilator during a breath.

A ventilation "mode", on the other hand, is a set of rules controlling how multiple subsequent breaths should be delivered. Modes may be mandatory, that is controlled by the ventilator, or spontaneous, that is that allow a breath to be delivered or controlled upon detection of a patient's effort to inhale, exhale or both. For example, a simple mandatory mode of ventilation is to deliver one breath of a specified mandatory breath type at a clinician-selected respiratory rate (e.g., one breath every 6 seconds). Until the mode is changed, ventilators will continue to provide breaths of the specified breath type as dictated by the rules defining the mode. For example, breath types may be mandatory mode breath types (that is, the initiation and termination of the breath is made by the ventilator) or spontaneous mode breath types (which refers to breath types in which the breath is initiated and terminated by the patient). Examples of breath types utilized in the spontaneous mode of ventilation include proportional assist (PA) breath type, volume support (VS) breath type, pressure support (PS) breath type, and etc. Examples of mandatory breath types include a volume control breath type, a pressure control breath type, and etc.

Positive pressure delivery during mechanical ventilation can be injurious to the lung. Therefore, measurements and methods that would allow for minimizing the lung injury have been utilized by mechanical ventilators to reduce lung injuries. Previously, studies showed that utilizing low tidal volume was likely to prevent ventilator-induced lung injury (VILI). However, newer studies have shown that low tidal volumes only increase the chance of patient survival (or reduce the likelihood VILI) if this low tidal volume is associated with decreases in patient drive pressure. Further, studies have shown that increases in patient drive pressure, particularly above 15 cm of $H_2O$, are strongly associated with decreased patient survival rates. As such, patient drive pressure may be a better mechanical ventilation parameter than tidal volume for survival prediction and/or ventilation control.

Patient drive is the pressure that is applied 'inside the lungs' causing them to inflate. This 'driving pressure' is what the lungs are exposed to in order to inflate them against the compliance of the lung. For a mechanically ventilated patient, the patient drive pressure can be calculated as the pressure above baseline pressure applied by the ventilator at the patient wye (i.e., Pwye–Pend exp), minus the pressure to overcome the artificial airway (i.e., RTUBE*QLUNG), minus the pressure created by the respiratory muscles (i.e., Pmus). Accordingly, the equation for calculating drive pressure is listed below:

$$P\text{drive}=P\text{wye}-P\text{end exp}-RTUBE \cdot QLUNG-P\text{mus}, \quad (EQ\ \#1)$$

where:
 Pdrive is patient drive pressure;
 Pwye is pressure at the wye;
 Pend exp is pressure at the end of exhalation;
 RTUBE is the resistance of the endotracheal tube or tracheostomy tube;
 QLUNG is lung flow; and
 Pmus, is muscle pressure.

During mandatory modes of ventilation, the patient is sedated. As such, during mandatory modes of ventilation, the muscle pressure of the patient is zero since the patient is passive. Accordingly, if an inspiratory pause is applied to the patient during the mandatory mode of ventilation, such that the pressure on either side of the artificial airway (endotracheal tube or tracheostomy tube) is the same, the lung flow (QLUNG) will be zero and the above Equation #1 simplifies to:

$$P\text{drive} = P\text{wye} - P\text{end exp}, \quad (EQ\ \#2).$$

However, in order for the above equation to work, the patient must be ventilated utilizing a mandatory mode of ventilation and the patient must be passive (such as sedated). As such, several ventilators are capable of calculating and displaying drive pressure during mandatory modes of ventilation on a passive patient with use of an inspiratory pause. However, if the patient is not passive, then the ventilator, even during a mandatory mode of ventilation, is not capable of calculating patient drive pressure. During a spontaneous mode of ventilation, the patient is not passive so the patient's muscle pressure varies throughout each breath and patient drive pressure is, therefore, a much more difficult calculation. Currently, the only ventilators that are capable of calculating drive pressure during a spontaneous mode of ventilation or during any mode of ventilation where the patient is not passive, requires invasive monitoring techniques.

Accordingly, the current disclosure describes a drive pressure (DP) breath type for ventilating a patient. The DP breath type (also referred to herein as drive pressure ventilation) is a spontaneous breath type that allows for the calculation of drive pressure that does not require invasive monitoring. To accomplish this goal, the DP breath type briefly interrupts and smoothly transitions from a base spontaneous breath subtype into a temporary proportional assist (PA) breath subtype for a predetermined period in response to a condition and then smoothly transitions back into the base spontaneous breath subtype. In some aspects, the DP breath type accomplishes the smooth transition by determining a percent support setting for the PA breath subtype based on the target settings of the base spontaneous breath subtype and/or based on non-invasively monitored/measured parameters. In other aspects, a predetermined percent support setting is utilized for the transition by the DP breath type. As such, ventilator systems and methods utilizing the DP breath type may adjust ventilator parameters and/or perform other actions based on a monitored drive pressure.

FIG. 1 is a schematic diagram illustrating an example of a ventilator 100 connected to a human patient 150. Ventilator 100 includes a pneumatic system 102 (also referred to as a pressure generating system 102) for circulating breathing gases to and from patient 150 via the ventilation tubing system 130, which couples the patient 150 to the pneumatic system 102 via an invasive (e.g., endotracheal tube, as shown) or a non-invasive (e.g., nasal mask) patient interface 180.

Ventilation tubing system 130 (or patient circuit 130) may be a two-limb (shown) or a one-limb circuit for carrying gases to and from the patient 150. In a two-limb embodiment, a fitting, typically referred to as a "wye-fitting", may be provided to couple a patient interface 180 (as shown, an endotracheal tube) to an inspiratory limb 132 and an expiratory limb 134 of the ventilation tubing system 130.

Pneumatic system 102 may be configured in a variety of ways. In the present example, pneumatic system 102 includes an expiratory module 108 coupled with the expiratory limb 134 and an inspiratory module 104 coupled with the inspiratory limb 132. Compressor 106 or other source(s) of pressurized gases (e.g., air, oxygen, and/or helium) is coupled with inspiratory module 104 and the expiratory module 108 to provide a gas source for ventilatory support via inspiratory limb 132.

The inspiratory module 104 is configured to deliver gases to the patient 150 according to prescribed ventilatory settings. In some embodiments, inspiratory module 104 is configured to provide ventilation according to various breath types, e.g., via a DP breath type, or via any other suitable breath types.

The expiratory module 108 is configured to release gases from the patient's lungs according to prescribed ventilatory settings. Specifically, expiratory module 108 is associated with and/or controls an expiratory valve for releasing gases from the patient 150.

The ventilator 100 may also include one or more non-invasive sensors 107 communicatively coupled to ventilator 100. Sensors are referred to herein as non-invasive when the sensors are located externally to patient. For example, sensors located in the patient wye 170, in the expiratory module 108, in the inspiratory module 104, or on the patient's finger are all external to the patient and are non-invasive. Sensors are referred to herein as invasive when the sensors are located within the patient or placed inside the patient's body, such as sensors located in an endotracheal tube, near a patient diaphragm, or on an esophageal balloon. While invasive sensors can provide great patient data or measurements, these sensors can often be hard to maintain or keep properly positioned. For example, an esophageal balloon can easily be knocked out of proper position in response to patient movement. Once moved, all of the data recorded from the sensors on the balloon are inaccurate. Further, if condensation or material corrupts the sensor and interferes with accurate measurements, the invasive sensor has to be removed from the body to service and/or clean it. Further, because invasive sensors are located within the patient, they usually require the patient to be sedated or undergo a surgical procedure for implantation or positioning adjustment. As such, invasive sensors are burdensome to the patient, hard to implant, hard to maintain, and hard to keep positioned when compared to non-invasive sensors. The embodiment of FIG. 1 illustrates a sensor 107 in pneumatic system 102.

Sensors 107 may communicate with various components of ventilator 100, e.g., pneumatic system 102, other sensors 107, processor 116, condition module 117, drive pressure module 118, treatment module 119, and/or any other suitable components and/or modules. In one embodiment, sensors 107 generate output and send this output to pneumatic system 102, other sensors 107, processor 116, condition module 117, drive pressure module 118, treatment module 119 and any other suitable components and/or modules. Sensors 107 may employ any suitable sensory or derivative technique for monitoring one or more patient parameters or ventilator parameters associated with the ventilation of a patient 150. Sensors 107 may detect changes in patient parameters indicative of patient triggering, for example. Sensors 107 may be placed in any suitable non-invasive location, e.g., within the ventilatory circuitry (excluding an endotracheal tube) or other devices communicatively coupled to the ventilator 100. Further, sensors 107 may be placed within the ventilatory circuitry or within components or modules of ventilator 100. For example, sensors 107 may be coupled to the inspiratory and/or expiratory modules for detecting changes in circuit pressure and/or flow. In other examples, sensors 107 may be affixed to the ventilatory tubing or may be embedded in the tubing itself. Additionally or alternatively, sensors 107 may be affixed or embedded in or near wye-fitting and/or in a non-invasive patient interface. Indeed, any non-invasive sensory device useful for monitoring changes in measurable parameters during ventilatory treatment may be employed in accordance with embodiments described herein. In some aspects, the ventilator 100 does not utilize any invasive sensors or sensory devices.

As should be appreciated, with reference to the Equation of Motion, ventilatory parameters are highly interrelated and, according to embodiments, may be either directly or indirectly monitored. That is, parameters may be directly monitored by one or more sensors 107, as described above, or may be indirectly monitored or estimated/calculated using a model, such as a model derived from the Equation of Motion:

$$Pmus = Pwye - Pend\exp-(RTUBE+Rrs)QLUNG-\frac{\int QLUNGdt}{Crs},$$  EQ #3 where:
Rrs is respiratory system resistance;
Crs is respiratory system compliance; and
∫QLUNGdt is lung flow integrated over time.

The pneumatic system 102 may include a variety of other components, including mixing modules, valves, tubing, accumulators, filters, etc. Controller 110 is operatively coupled with pneumatic system 102, signal measurement and acquisition systems, and an operator interface 120 that may enable an operator to interact with the ventilator 100 (e.g., change ventilator settings, select operational modes, view monitored parameters, etc.).

In one embodiment, the operator interface 120 of the ventilator 100 includes a display 122 communicatively coupled to ventilator 100. Display 122 provides various input screens, for receiving clinician input, and various display screens, for presenting useful information to the clinician. In one embodiment, the display 122 is configured to include a graphical user interface (GUI). The GUI may be an interactive display, e.g., a touch-sensitive screen or otherwise, and may provide various windows and elements for receiving input and interface command operations. Alternatively, other suitable means of communication with the ventilator 100 may be provided, for instance by a wheel, keyboard, mouse, or other suitable interactive device. Thus, operator interface 120 may accept commands and input through display 122. Display 122 may also provide useful information in the form of various ventilatory data regarding the physical condition of a patient 150. The useful information may be derived by the ventilator 100, based on data collected by a processor 116, and the useful information may be displayed to the clinician in the form of graphs, wave representations, pie graphs, text, or other suitable forms of graphic display. For example, patient data may be displayed on the GUI and/or display 122. Additionally or alternatively, patient data may be communicated to a remote monitoring system coupled via any suitable means to the ventilator 100. In one embodiment, the display 122 may display one or more of an alert, a current drive pressure, a past drive pressure, a drive pressure graph, a recommendation, a drive pressure breach of a threshold, a ventilation parameter change, a current patient effort, a diaphragmatic pressure, a patient respiratory compliance, a patient respiratory resistance, a desired drive pressure range, a trigger sensitivity, a condition, a tidal volume, a flow, a pressure, a target setting, a breath type, a ventilation mode, and/or etc.

Controller 110 is a command and control computing devices and may include memory 112, one or more processors 116, storage 114, and/or other components of the type commonly found in command and control computing devices. Controller 110 may further include a condition module 117, a drive pressure module 118, and/or a treatment module 119 as illustrated in FIG. 1. A module as used herein may also refer to a command and control computing device. A module as used herein may refer to memory, one or more processors, storage, and/or other components of the type commonly found in command and control computing devices. In alternative embodiments, the condition module 117, the drive pressure module 118, and the treatment module 119 may be located in other components of the ventilator 100, such as the pressure generating system 102 (also known as the pneumatic system 102).

The memory 112 includes non-transitory, computer-readable storage medium that stores software that is executed by the processor 116 and which controls the operation of the ventilator 100. In an embodiment, the memory 112 includes one or more solid-state storage devices such as flash memory chips. In an alternative embodiment, the memory 112 may be mass storage connected to the processor 116 through a mass storage controller (not shown) and a communications bus (not shown). Although the description of computer-readable media contained herein refers to a solid-state storage, it should be appreciated by those skilled in the art that computer-readable storage media can be any available non-transitory medium that can be accessed by the processor 116. That is, computer-readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

The inspiratory module 104 receives a selected DP breath type from the controller 110. The DP breath type utilizes a mix of two different breath types (referred to herein as breath subtypes) and smoothly transitions between the two different breath types. The two different breath types utilized within the DP breath type are referred to herein as a base breath subtype and a temporary breath subtype that is triggered upon the detection or occurrence of a condition. The base breath subtype is any spontaneous breath type other than the PA breath type, such as a PS or VS breath type. In some aspects, the base spontaneous breath subtype is predetermined for the DP breath type. In other aspects, the base spontaneous breath subtype is selected by the clinician. Depending upon the base spontaneous breath subtype, other inputs, such as a target setting, may be required from the clinician for operating the DP breath type. A target setting as utilized herein refers to a setting that has to be input for a breath type or breath subtype to function or work. For example, if the base spontaneous breath subtype is a PS breath type, the ventilator 100 may require a target pressure input from the clinician. For example, if the base spontaneous breath subtype is a VS breath type, ventilator 100 may require a target tidal volume input from the clinician. However, other inputs, such as patient interface type, ventilation tubing system size, PEEP levels, and/or etc. may also be required from the clinician for operating the DP breath type depending upon the type of ventilator and/or the base spontaneous breath subtype. The temporary breath subtype is a PA breath type. When the PA breath type is being utilized as the temporary breath subtype during a DP breath type, the PA breath type is referred to herein a PA breath subtype. As such, while the use of different breath types, such as PA, PS, VS are discussed herein, these breath types are not being implemented, but instead are being utilized as breath subtype or portion within the DP breath type. During the DP breath type, the controller 110 sends instructions to the inspiratory module 104 and/or the expiratory module 108 for delivering the base spontaneous breath subtype while the condition module 117 of the controller 110 monitors for a condition.

Initiation and execution of a DP breath type requires detection of an inspiratory trigger. In some aspects, a patient trigger is calculated based on a measured or monitored patient inspiration flow. Any suitable type of triggering detection for determining a patient trigger may be utilized by the ventilator 100, such as nasal detection, diaphragm detection, and/or brain signal detection. Further, the ventilator 100 may detect patient triggering via a pressure-monitoring method, a flow-monitoring method, direct or indirect measurement of neuromuscular signals, or any other suitable method. Sensors 107 suitable for this detection may include any suitable sensing device as known by a person of skill in the art for a ventilator.

According to an embodiment, a pressure-triggering method may involve the ventilator 100 monitoring the circuit pressure, and detecting a slight drop in circuit pressure. The slight drop in circuit pressure may indicate that the patient's respiratory muscles are creating a slight negative pressure that in turn generates a pressure gradient between the patient's lungs and the airway opening in an effort to inspire. The ventilator 100 may interpret the slight drop in circuit pressure as a patient trigger and may consequently initiate inspiration by delivering respiratory gases.

Alternatively, the ventilator 100 may detect a flow-triggered event. Specifically, the ventilator 100 may monitor the circuit flow, as described above. If the ventilator 100 detects a slight drop in the base flow through the exhalation module during exhalation, this may indicate, again, that the patient 150 is attempting to inspire. In this case, the ventilator 100 is detecting a drop in bias flow (or baseline flow) attributable to a slight redirection of gases into the patient's lungs (in response to a slightly negative pressure gradient as discussed above). Bias flow refers to a constant flow existing in the circuit during exhalation that enables the ventilator 100 to detect expiratory flow changes and patient triggering.

In response to a detection of a patient trigger, the controller 110 sends instruction to the inspiratory module 104 to deliver breathing gas to the patient based on the parameters of DP breath type.

During ventilation with the base spontaneous breath subtype, the condition module 117 monitors input to determine the occurrence of one or more conditions. In some aspects, the condition module 117 monitors the measurements from the non-invasive sensors. In other aspects, the condition module 117 monitors other received ventilator data or calculations to determine the occurrence of the condition. In some aspects, the condition may be any event that is indicative of a change in patient respiratory system compliance and/or patient respiratory system resistance, such as a predetermined pressure differential, volume differential, a tidal volume differential, a specific flow waveform shape, a specific volume waveform shape, a specific pressure waveform shape, a predetermined change in pressure, a predetermined change in flow, a predetermined change in tidal volume and/or etc. For example, the condition may be a change in non-invasively monitored flow, pressure, and/or of volume of at least 25%. In other aspects, the condition is an expiration of a set period or predetermined number of breaths, since the last PA breath subtype switch or since the start of the last PA breath subtype. For example, the condition may be the expiration of 30, 60, 90, or 120 minutes or the occurrence of 400, 300, or 200 breaths since the last temporary switch into the PA breath subtype or the start of the last PA breath subtype. In other examples, the condition module 117 monitors for the following condition to occur: 1) expiration of 1 hour since the last PA breath subtype; or 2) a 25% change in one of non-invasively measured pressure, flow, or tidal volume during the base spontaneous breath subtype. If the DP breath type was just initialized, the conditions discussed above may be monitored from the start of ventilation or the start of the DP breath type instead of since the last temporary switch into the PA breath subtype or the start of the last PA breath subtype. If the condition module 117 detects a condition, the condition module 117 of the controller 110 determines a percent support setting and sends instructions to the pressure generating system 102 to provide a short temporary switch into a PA breath subtype utilizing the determined percent support setting.

In some aspects, the condition module 117 determines a percent support setting by utilizing a predetermined or preset percent support setting. In other aspects, the condition module 117 determines a percent support setting based on a target setting for the base spontaneous breath subtype. For example, if the target pressure for the PS breath type is 10 cm $H_2O$, then the condition module 117 will determine a percent supporting setting to achieve approximately the same pressure level. In another example, if the target volume for a VS breath type is 400 ml, then the condition module 117 will determine a percent support setting to achieve approximately the same volume level. In other aspects, the percent setting is determined by the condition module 117 based on outputs from the non-invasive sensor. For example, if inspiratory pressure measurement is 9.8 cm $H_2O$ from inspiratory pressure sensor, then the condition module 117 will determine a percent support setting to achieve approximately the same pressure level. In further aspects, the condition module 117 may utilize additional ventilator parameters or inputs to the target setting and/or the outputs from the non-invasive sensor to determine a percent support setting, such as mask type, patient circuit diameter, and etc.

The PA breath subtype is an effort-based breath type that dynamically determines the amount of ventilatory support to deliver based on a continuous estimation/calculation of patient effort and respiratory characteristics. Patient effort as discussed in the PA breath type is not a muscle pressure (Pmus). In contrast, the patient effort during the PA breath type refers to resistive and elastic pressure drops. The resulting dynamically generated profile is computed in real- or quasi-real-time and used by the ventilator as a set of points for control of applicable parameters.

Initiation and execution of an effort-based breath type, such as PA breath type or PA breath subtype, has two operation prerequisites: (1) detection of an inspiratory trigger; and (2) detection and measurement of an appreciable amount of patient respiratory effort to constitute a sufficient reference above a ventilator's control signal error deadband. Advanced, sophisticated triggering technologies detect initiation of inspiratory efforts efficiently. Patient effort is calculated based on measured patient inspiration flow. Patient effort is utilized to calculate a target airway pressure for the inspiration. The delivered airway pressure as used herein is the airway pressure measured at the ventilator-patient interface. The target airway pressure is resistive pressure (Presistive) plus elastic pressure (Pelastic) plus positive end exhalation pressure (PEEP), where Presistive and Pelastic are scaled by the percent support setting.

A PA breath type or subtype refers to a type of ventilation in which the ventilator acts as an inspiratory amplifier that provides pressure support based on the patient's effort. Usually, the degree of amplification (the "percent support setting") during a PA breath type is set by an operator or clinician, for example as a percentage based on the patient's effort. However, during the DP breath type, the condition module 117 determines the percent support setting provided during the PA breath subtype.

In one implementation of a PA breath subtype, the ventilator may continuously monitor the patient's instantaneous inspiratory flow and instantaneous net lung volume, which are indicators of the patient's inspiratory effort. These signals, together with ongoing estimates of the patient's lung compliance and lung/airway resistance and the Equation of Motion $$\left(Pmus = Pwye - Pend\exp-(RTUBE+Rrs)QLUNG - \frac{\int QLUNGdt}{Crs}\right),$$

allow the ventilator to estimate/calculate a patient effort and derive therefrom a target airway pressure to provide the support that assists the patient's inspiratory muscles to the degree selected by the operator as the percent support setting. In this equation, the patient effort is inspiratory muscle pressure and is negative. The percent support setting as determined by the condition module 117 divides the total work of breathing calculated between the patient and the ventilator.

Unlike other spontaneous breath subtypes, the PA breath subtype can calculate compliance and resistance without having to utilize an invasive sensor. As such, the PA breath subtype is a spontaneous breath type that is able to calculate dynamic respiratory system compliance and respiratory system resistance. In other spontaneous breath subtypes, an invasive sensor located in an esophageal balloon is needed. However, as discussed above, an esophageal balloon can easily become dislodged if the patient moves affecting sensor accuracy, is highly invasive to implant, and/or is uncomfortable for a spontaneously breathing patient. Due to the disruptive nature of the esophageal balloon, the esophageal balloon is rarely utilized during a spontaneous breath subtype.

Due to the unique configuration of the PA breath subtype, the PA breath subtype is capable of determining a patient respiratory system compliance and/or resistance in an end exhalation hold of 300 ms or 0.3 seconds, which will usually go unnoticed by a spontaneously breathing patient. In a typical PA breath type, this 300 ms end expiratory hold is provided intermittently at random. During the DP breath type, the 300 ms end expiratory hold is provided in the first, second, third, or fourth breath of the temporary PA breath subtype portion of the DP breath type. Any additional 300 ms holds are provided after a predetermined number of breaths or after a set time period during the PA breath subtype. In other words, the PA breath subtype does not provide the 300 ms end expiratory hold at random but instead at predetermined intervals. As such, the DP breath type is able to calculate patient respiratory compliance and patient respiratory system resistance without having to utilize an invasive sensor measurement. The DP breath type utilizes the following equation to determine patient respiratory system compliance:

$$C_{RAW}=(V_{LUNG}/\text{Pressure\_delta}).$$

The DP breath type utilizes the following equation to determine patient respiratory system resistance:

$$R_{RAW}=R_{RAW+ET}-R_{ET},$$

where:
$R_{RAW}$ is patient respiratory system resistance;
$R_{RAW+ET}$ is the combined resistance of the patient respiratory system and the endotracheal tube/tracheostomy tube resistance; and
$R_{ET}$ is endotracheal tube/tracheostomy tube resistance.
$R_{RAW+ET}$ is the difference in lung pressure and wye pressure divided by the estimated lung flow. The lung pressure is based upon the lung pressure at the beginning of exhalation minus exhaled volume times the elastance. Wye pressure is estimated as the measured pressure inside the ventilator compensated for inspiratory limb resistance.

During the PA breath subtype, the drive pressure module 118 calculates patient respiratory resistance and/or compliance based on non-invasive sensor output. The condition module 117 provides the PA breath subtype for at least one breath. In some aspects, the condition module 117 provides the PA breath subtype for at least three breaths. In some aspects, the condition module 117 provides the PA breath subtype until a predetermined number of patient respiratory compliance and/or resistance measurements have been made by the ventilator 100. In some aspects, the condition module 117 provides the PA breath subtype until at least two or three patient respiratory compliance and/or resistance measurements have been made by the ventilator 100. In other aspects, the condition module 117 provides the PA breath subtype until at least one, two, three, four, or five patient respiratory compliance and/or resistance measurements have been made by the ventilator 100. The predetermined number of patient respiratory compliance and/or resistance measurements can be completed in 1 breath, 2 breaths, 3 breaths, 5 breaths, 7 breaths, 8 breaths, 10 breaths, 12 breaths, 15 breaths, 20 breaths, 25 breaths or 30 breaths. In other aspects, a predetermined number of patient respiratory compliance and/or resistance measurements can be completed by the condition module 117 in 4 to 12 breaths.

After the temporary PA breath subtype portion has been completed (e.g., the predetermined number of patient respiratory compliance and/or resistance measurements have been made by the ventilator 100), the condition module 117 switches the ventilation of the patient back to the previously utilized base spontaneous breath subtype.

After the return to the previously utilized base spontaneous breath subtype, the drive pressure module 118 monitors respiratory data of the patient, such as the non-invasive sensor output. In some aspects, the drive pressure module 118 estimates a dynamic drive pressure waveform of the patient during the spontaneous breath subtype based on the respiratory data and the respiratory system compliance and/or compliance. Next, the drive pressure module 118 calculates a drive pressure of the patient during the spontaneous breath subtype utilizing the respiratory system compliance and/or the respiratory system resistance, and the respiratory data. The drive pressure calculated by the drive pressure module 118 can be dynamic and/or static.

In some aspects, equations (1) and (3) can be combined to get the following drive pressure equation:

$$P\text{drive} = Rrs Q\text{LUNG} + 1/Crs \int Q\text{LUNG} dt, \quad \text{EQ \#4.}$$

If equation #4 above is evaluated at the end of the inspiratory phase, and QLUNG is assumed to be zero (e.g., at the transition point between inspiration and exhalation), the integral of QLUNG is the tidal volume, Vt. Based on these assumptions, a static drive pressure is calculated by the drive pressure module 118 of control 110 by utilizing the following equation:

$$P\text{drive} = 1/Crs Vt = Vt/Crs, \quad \text{EQ \#5.}$$

In further aspects, a dynamic drive pressure is calculated by the drive pressure module 118 of control 110 by utilizing the following equation:

$$P\text{mus} = P\text{wye} - P\text{end exp} - (R\text{TUBE} + Rrs)Q\text{LUNG} - 1/Crs \int Q\text{LUNG} dt, \quad \text{EQ \#6}$$

where:
Pmus=respiratory muscle pressure;
Pwye=pressure at the patient wye;
Pend exp=pressure at the end of the expiratory phase;
RTUBE=resistance of the artificial airway;
Rrs=patient respiratory resistance;
QLUNG=lung flow; and
Crs=compliance of the respiratory system.

As can be seen from the above equations, at the end of the inspiratory phase where QLUNG=0 and ∫QLUNGdt=tidal volume, dynamic and static drive pressure are the same. However, when the lung flow is non-zero, the driving pressure includes a component related to the resistance of the patient respiratory system. Under some conditions, this can result in the maximum driving pressure being higher than the driving pressure at the end of the inspiratory phase. In these situations, the use of the driving pressure at the end of inspiration (or static drive pressure) may not fully represent the impact of the ventilator 100 on lung injury. As such, the dynamic drive pressure measurement is a better or more accurate measurement for determining and/or preventing lung injury than the static drive pressure measurement.

The drive pressure module 118 measures the drive pressure repeatedly throughout a breath. In some aspects, the drive pressure module 118 measures drive pressure every servo cycle, such as every 2 milliseconds, 5 millisecond, or 10 milliseconds. The servo cycle is the amount of time required by the processor 116 or controller 110 of the ventilator 100 to perform a calculation in response to a received measured pressure or flow. In some aspects, the sensors 107 send output or measurements every servo cycle.

The drive pressure module 118 communicates the drive pressure to other modules, such as the treatment module 119 and condition module 117, controller 110, the pneumatic system 102, and/or the display 122.

The treatment module 119 performs an action in response to receiving the drive pressure. The action may include generating a display of the drive pressure, evaluating the drive pressure, generating an alert based on the drive pressure, providing a recommendation based on the drive pressure, and/or changing ventilator parameters based on the drive pressure. For example, the treatment module 119 may send instruction to the display to display 122 a determined drive pressure. In other aspects, the treatment module may generate a graph of the drive pressure, such as a waveform or bar graph of the drive pressure. For instance, the treatment module 119 may generate a graph or waveform of drive pressure versus time.

In some aspects, the treatment module 119 evaluates the drive pressure by comparing the drive pressure to a threshold. If the treatment module 119 determines that the drive pressure breaches the threshold, the treatment module 119 performs an action in response to this determination. As discussed above, the action may include a display of the drive pressure and/or the breach, generating an alert based on the breach, providing a recommendation based on the breach, and/or changing ventilator parameters based on the breach. If the treatment module 119 determines that the drive pressure does not breach the threshold, the treatment module 119 continues to evaluate the received drive pressures from the drive pressure module 118. In further aspects, if the treatment module 119 determines that the drive pressure does not breach the threshold, the treatment module 119 may also provide a recommendation to the clinician based on the drive pressure meeting the threshold.

The drive pressure threshold may be a drive pressure of 15 cm of $H_2O$ or less, a drive pressure of 10 cm of $H_2O$ or less, or a drive pressure of 5 cm of $H_2O$ to 15 cm of $H_2O$. This list is exemplary and is not meant to be limiting. Any suitable drive pressure range for optimal patient ventilation may be utilized by the treatment module 119, controller 110, and/or ventilator 100. The threshold may be predetermined, selected by the ventilator based on other patient information, or selected or input by a clinician.

In response to a drive pressure or a breach of a threshold by the drive pressure, the treatment module 119 may generate an alert. The alert may be a visual, audio, or any other type of sensory notification that notifies a clinician that the patient's drive pressure has breached a predetermined threshold. In response to a drive pressure meeting a threshold, or a breach of a threshold, the treatment module 119 may provide a recommendation. The recommendation may be changes to ventilator parameters, such as target settings, other ventilator settings, changes in breath type, changes in breath subtype, and/or changes in ventilator mode. For example, if the drive pressure exceeds a threshold, such as is greater than 15 cm of $H_2O$, the treatment module 119 may recommend a decrease in tidal volume, a decrease in flow, a decrease in pressure, an increase in PEEP, and/or a decrease in PEEP to try and bring the drive pressure within the desired levels. For example, if the drive pressure exceeds a threshold, such as is less than 2 cm of $H_2O$, the treatment module 119 may recommend an increase in tidal volume, an increase in flow, an increase in pressure, and/or a increase in PEEP because such changes may be beneficial for the patient and have no or very low risk of causing lung injury. Alternatively, the treatment module 119 may automatically modify the ventilation parameters listed above based on drive pressure or the result of a comparison of drive pressure to a threshold. The ventilation parameter may include a target setting, oxygen percentage, rise time, trigger sensitivity, peak flow rate, peak inspiratory pressure, tidal volume, and/or PEEP. In some aspects, the treatment module 119 may adjust ventilation parameters to maintain the drive pressure within a target range, such as the threshold. An automatic change in ventilation parameter may be sent by treatment module 119 to the display 122 or other modules to notify the clinician of the change.

As discussed above, method 200 illustrates a method for drive pressure ventilation of a patient with a ventilator. Accordingly, method 200 ventilates a patient with a DP breath type. Method 200 provides a spontaneous breath type that allows for the calculation of dynamic drive pressure and does not require invasive monitoring. To accomplish this goal, the method 200 briefly interrupts and smoothly transitions from a base spontaneous breath subtype, other than a PA breath subtype, into the PA breath subtype in response to a condition and then smoothly transitions back into the base spontaneous breath subtype when a patient respiratory system compliance and/or resistance has been calculated. Method 200 accomplishes the smooth transition by determining a percent support setting for the PA breath subtype. As such, method 200 may adjust ventilator parameters and/or perform other actions based on a monitored dynamic drive pressure.

As illustrated, method 200 includes a spontaneous ventilation operation 201. During the spontaneous ventilation operation 201, the ventilator ventilates the patient utilizing a spontaneous breath subtype. The spontaneous breath subtype is any spontaneous breath type other than a PA breath type.

As illustrated, method 200 includes a spontaneous collection operation 202. During the spontaneous collection operation 202, the ventilator collects and analyzes non-invasive sensor output during the spontaneous breath subtype. In other words, during spontaneous collection operation 202, the ventilator non-invasively monitors respiratory data of the patient. Non-invasive sensor output or respiratory data refers to the output or measurements generated by non-invasive sensors. As such, in some aspects, during spontaneous collection operation 202, the ventilator collects flow rate, tidal volume, and/or pressure measurements from non-invasive sensors located in the ventilator 100 and/or ventilation tubing system 130. In some aspects during spontaneous collection operation 202, the ventilator 100 estimates a pressure or flow at the wye 170 based on an analysis of the non-invasive sensor output. In other aspects, other parameters are derived by the ventilator 100 during spontaneous collection operation 202 based on analysis of the of the non-invasive sensor output.

During operations 201 and 202, the ventilator analyzes the non-invasive sensor output or respiratory data to detect a patient effort. During operations 201 and 202, the ventilator delivers inspiratory gas to the patient with the ventilator in response to a detected patient effort. The inspiratory gas is delivered according to the spontaneous breath subtype.

At DP operation 204, a drive pressure of the patient is calculated or estimated during the spontaneous breath subtype utilizing a calculated or estimated compliance measurement and/or resistance measurement determined during the last PA breath subtype and the output from the sensors during the spontaneous breath subtype. The calculation and/or estimation of the compliance measurement and/or resistance measurement is discussed in more detail below and performed during operations 212 and 214. In some aspects, the ventilator during DP operation 204 may calculate or estimate the muscle pressure of the patient during the spontaneous breath subtype based on the compliance measurement and/or resistance measurement. During DP operation 204, the ventilator calculates or estimates a dynamic drive pressure. For example, as discussed above, the ventilator during DP operation 204 may calculate or estimate the dynamic drive pressure by utilizing Equation #6 listed above. In some aspects, the ventilator during DP operation 204 is also capable of calculating or estimating static drive pressure by utilizing Equation #5 listed above.

Method 200 also includes a determination operation 206. At determination operation 206, the ventilator determines if a condition occurred. In some aspects, the ventilator during determination operation 206 monitors the non-invasive sensor output to determine if the condition has occurred. In other aspects, the ventilator during determination operation 206 monitors the number of delivered breath or the passage of time to determine if a condition has occurred. If the ventilator determines that the condition occurred at determination operation 206, the ventilator selects to perform support setting operation 208. If the ventilator determines that the condition did not occur during determination operation 206, the ventilator selects to perform action operation 220. The condition may be the expiration of a predetermined amount of time, the delivery of a predetermined number of breaths, and/or a change in one or more monitored parameters that indicates that a change in patient respiratory system compliance and/or resistance has occurred. In some aspects, the condition is a change in monitored pressure, monitored tidal volume, or monitored flow of at least 25%. In other aspects, the condition is expiration of 1 hour from the last use of the PA breath subtype without a change in monitored pressure, monitored tidal volume, or monitored flow of at least 25% since the last PA breath subtype. In further aspects, the condition is the delivery of 200 breaths from the last use of the PA breath subtype without a change in monitored pressure, monitored tidal volume, or monitored flow of at least 25% since the last PA breath subtype.

As illustrated, method 200 includes support setting operation 208. At support setting operation 208 the ventilator determines a percent support setting for a PA breath subtype. In some aspects, at support setting operation 208, the ventilator utilizes a predetermined support setting. In other aspects, at support setting operation 208 the ventilator selects a support setting based on at least one of a target setting from the spontaneous breath subtype or the non-invasively measured respiratory data collected during the spontaneous breath subtype. In further aspects, the ventilator during support setting operation 208 determines other settings for the PA breath subtype. For example, a PEEP level for the PA breath subtype may be set based on a PEEP level utilized in the spontaneous breath subtype.

Next, switch operation 210 is performed by the ventilator. At switch operation 210 the ventilator automatically and temporarily switches from the spontaneous breath subtype into the PA breath subtype for at least one breath utilizing the determined or calculated percent support setting. In some aspects, at switch operation 210 the ventilator automatically and temporarily switches from the spontaneous breath subtype into the PA breath subtype for at least three breaths utilizing the determined or calculated percent support setting. The PA breath subtype is performed for at least one breath, at least two breaths, or at least three breaths. In some aspects, the PA breath subtype is delivered by the ventilator during switch operation 210 until at least one patient respiratory system compliance and/or resistance measurement has been obtained. In some aspects, the PA breath subtype is delivered by the ventilator during switch operation 210 until at least two different patient respiratory system compliance and/or resistance measurements have been obtained. In some aspects, the PA breath subtype is delivered by the ventilator during the switch operation 210 until 5, 4, 3, or 2 patient respiratory system compliance and/or resistance measurements have been obtained. As such, the ventilator may deliver ventilation utilizing the PA breath subtype for at most 4 breaths, 8 breaths, 10 breaths, 12 breaths, 15 breaths, 20 breaths, 30 breaths, 40 breaths, or 50 breaths.

Accordingly, method 200 also includes PA collect and analyze operation 212. The ventilator during the PA collect and analyze operation 212, collects and analyzes the non-invasively measured respiratory data during the PA breath subtype. Next, a compliance operation 214 is performed by the ventilator. During the compliance operation 214, the ventilator calculates or estimates the patient respiratory system compliance and/or resistance based on the non-invasively measured respiratory data taken during the PA breath subtype during the PA collect and analyze operation 212. If multiple patient respiratory system compliance and/or resistance measurements are taken by the ventilator during compliance operation 214, the ventilator determines a compliance measurement and/or a resistance measurement based on these multiple measurements. For example, if multiple patient respiratory system compliance measurements are taken, the ventilator may average the measurements or select the middle or last obtained measurement to be utilized as the PA breath subtype calculated compliance measurement for use during DP operation 204.

Method 200 also includes a return operation 216. At return operation 216 the ventilator switches from the PA breath subtype back to the previously utilized spontaneous breath subtype. As discussed above, the ventilator returns the spontaneous breath subtype after a predetermined number of patient respiratory system compliance or resistance measurements have been obtained during the PA breath subtype, after a predetermined number of breaths, or after a predetermined amount of time. Next, spontaneous ventilation operation 201 is performed again.

Method 200 also includes action operation 220. At action operation 220, the ventilator performs an action based on drive pressure. The action may include generating a display of the drive pressure, evaluating the drive pressure, generating an alert based on the drive pressure, providing a recommendation based on the drive pressure, and/or changing ventilator parameters based on the drive pressure. In some aspects, the ventilator may generate a graph of the drive pressure for display during action operation 220, such as a waveform or bar graph of the drive pressure. In some aspects, the ventilator evaluates the drive pressure by comparing the drive pressure to threshold during action operation 220. If the ventilator determines that the drive pressure breaches the threshold during action operation 220, ventilator performs an action in response to this determination. As discussed above the action may include a display of the drive pressure and/or the breach, generating an alert based on the breach, providing a recommendation based on the breach, and/or changing ventilator parameters based on the breach. If the ventilator determines that the drive pressure does not breach the threshold during action operation 220, the ventilator continues to evaluate the calculated or estimated drive pressure. In further aspects, if the ventilator during action operation 220 determines that the drive pressure does not breach the threshold, the ventilator may also provide a recommendation to the clinician based on the drive pressure meeting the threshold.

In response to a drive pressure or a breach of a threshold by the drive pressure, the ventilator may generate an alert during action operation 220. In response to a drive pressure meeting a threshold, or a breach of a threshold, the ventilator may provide a recommendation. Alternatively, the ventilator during action operation 220 may automatically modify the ventilation parameters listed above based on drive pressure or the result of a comparison of drive pressure to a threshold.

Figure 2:
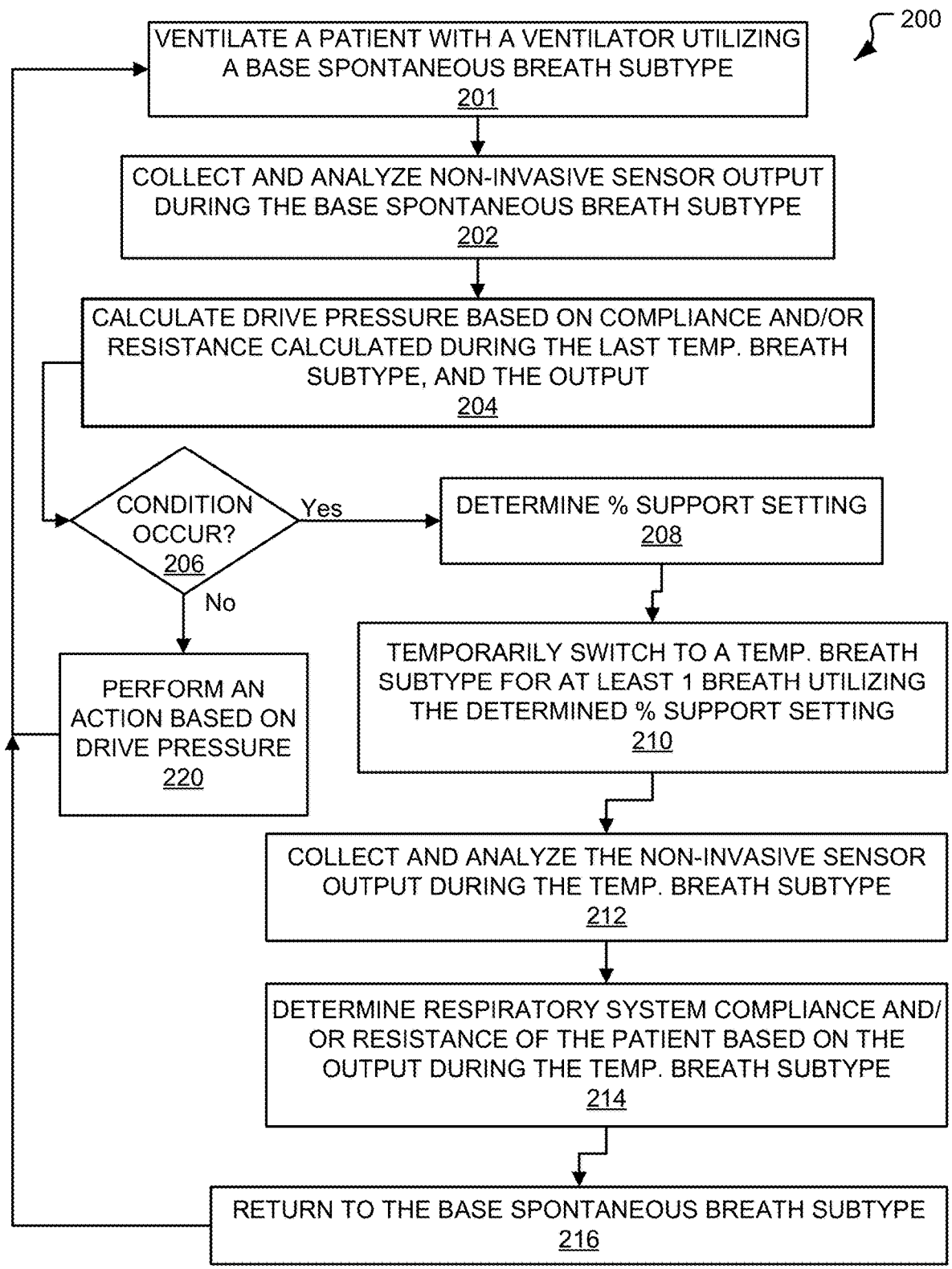
FIG. 2 is flow a diagram illustrating an example of a method for ventilating a patient on a ventilator in a drive pressure breath type, in accordance with aspects of the invention.

In some embodiments, a microprocessor-based ventilator that accesses a computer-readable medium having computer-executable instructions for performing the method of ventilating a patient with a medical ventilator is disclosed. This method includes repeatedly performing the steps disclosed in method 200 above and/or as illustrated in FIG. 2.

In some aspects, method 200 is performed by the ventilator 100 described above with reference to FIG. 1.

Figure 3:
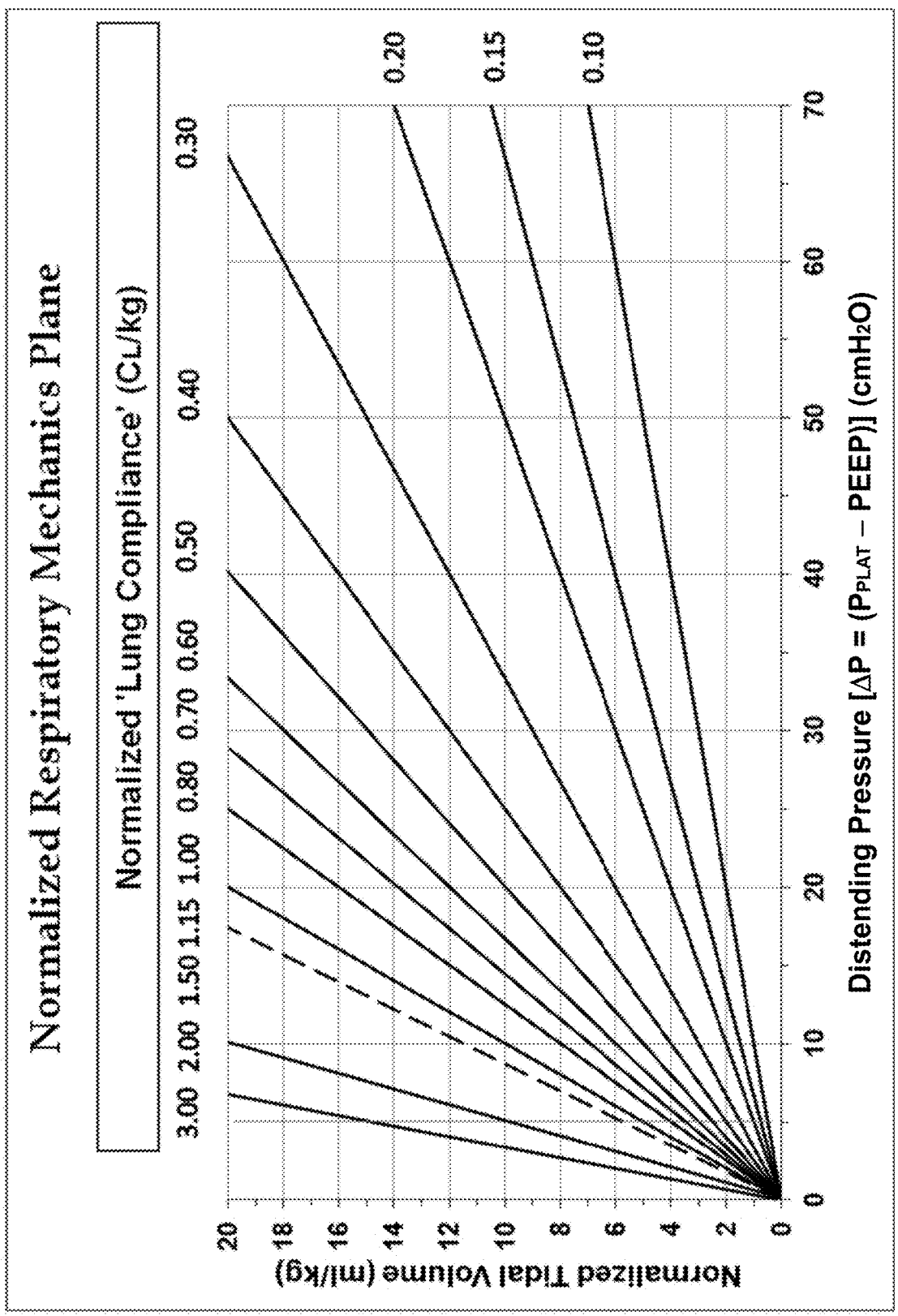
FIG. 3 is a chart illustrating an example of a normalized respiratory mechanics plane in accordance with aspects of the disclosure.
Figure 4:
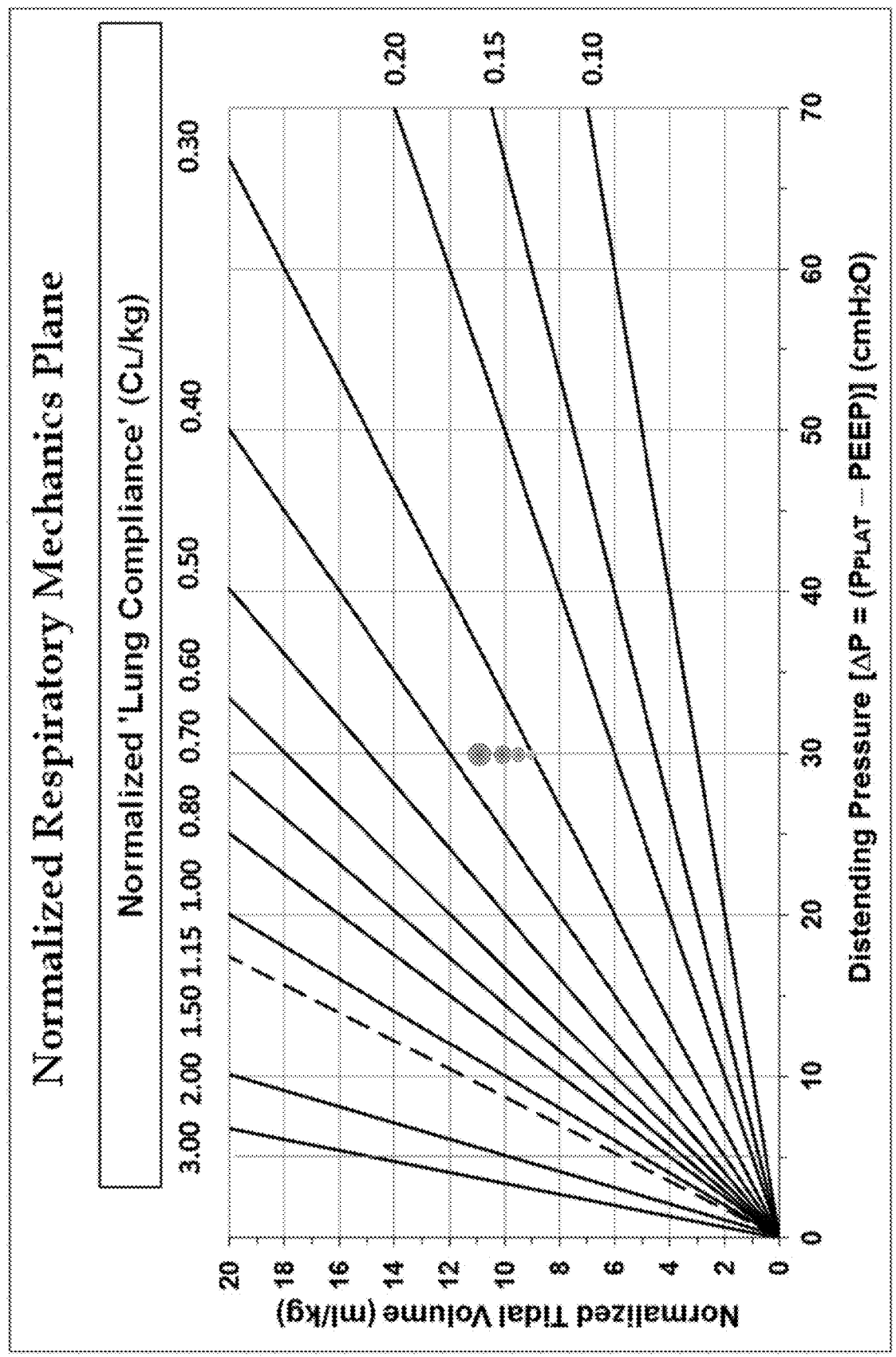
FIG. 4 is a chart illustrating an example of a normalized respiratory plane with provided patient trend line in accordance with aspects of the disclosure.

In another example, FIG. 3 is a chart illustrating a normalized respiratory mechanics plane (R-M Plane). FIG. 3 depicts the relationship between tidal volume (ml) and distending pressure ($\Delta P$ in $cmH_2O$). Distending pressure is calculated by subtracting the Positive End Expiratory Pressure (PEEP) from Plateau Pressure ($P_{PLAT}$), as illustrated by the X-axis of FIG. 3. In the context of patient ventilation, the following equation would operationalize the relationship: $V_T = \Delta P * C_L$, where $C_L$ represents the compliance (elasticity) of the patient lung-thorax system. The units of $C_L$ for FIGS. 3 and 4 are volume/pressure or $ml/cmH_2O$. Thus, if $C_L$ is known, the volume (ml) is found by multiplying $C_L$ by $\Delta P$. An examination of the equation $V_T = \Delta P * C_L$ reveals that $C_L$ becomes a constant with the units of $V_T/\Delta P$. i.e., $C_L$ is visualized as the positive slope of a line originating at 0,0, rising linearly up and to the right (should a separate slide be made). With a simple transformation of the units for the Y-axis, volume/predicted body weight (PBW) (the volume units for lung protective ventilation (ml/kg) and likewise expressing $C_L$ as $C_L/kg$ provides the chart illustrated in FIG. 3. FIG. 3 assumes the following:

1) The term ml/kg applied to all patients is valid and
2) The term $C_L/kg$ applied to all patients is also valid.

As such, the following can be stated (where $V_L$ is lung volume):

1) If $V_L/kg$ and $\Delta P$ are known, $C_L/kg = (V_L/kg)/\Delta P$;
2) If $V_L/kg$ and $C_L/kg$ are known, $\Delta P = (V_L/kg)/(C_L/kg)$; and
3) If $\Delta P$ and $C_L/kg$ are known, $V_L/kg = \Delta P * C_L/kg$.

Accordingly, any matched pair of coordinates for ml/kg and $\Delta P$ on FIG. 3 locates a unique point on the R-M Plane and that point lies on a line whose slope is $\approx C_L/kg$. Furthermore, all such matched coordinates whose ratio is equivalent ($\approx$) will also lie on that $C_L/kg$ slope. Recognizing that valid estimates for $\Delta P$ and $V_L/kg$ are available, the intersection of orthogonal projections of these two values identifies a probable estimate of the patient's current $C_L/kg$. A current estimate of a patient's actual $C_L$ is found by multiplying the normalized value by the patient's estimated PBW.

Given the structure of the R-M Plane, it's now possible to indicate how the patient's status can be monitored and identified, either by a software algorithm or by using boundary conditions set by the clinician. If the clinician were interested in maintaining lung-protective ventilation, upper and lower, horizontal boundaries would alert when $V_T/kg$ were too low or too high. Ventilator notifications could identify key changes and suggest corrections. A patient with ARDS might be decompensating with ever worsening compliance. Boundary violations could notify the clinician of this occurring.

In another aspect, a feature of the recurring points could be utilized with FIG. 3, to indicate the trajectory the patient's change as illustrated in FIG. 4. FIG. 4 is a chart illustrating a normalized respiratory mechanics plane with provided patient temporal status. The connection between sequential points would indicate rate of change and a notification could be provided by the ventilator to the clinician based on this rate of change. In FIG. 4 the repeated values for $V_T/kg$, $\Delta P$ and $C_L/kg$ are captured and processed every 5 minutes or so. At the end of each interval, software analyzes the patient's sensor data and indicates the patient's location on the R-M Plane. Identical sets of values would produce equivalent points. However, as shown in FIG. 4, if a new point differed by X from the last one, a new point whose structure/identity would differ from the last one is plotted on the chart. In some aspects, each point is time stamped on the chart. The three vertical array points, illustrated in FIG. 4, indicate that the insufflation pressure remained constant but the patient's $C_L$ was increasing coincident with increasing $V_L$. Given that the sequential values for $V_T$/kg, $\Delta P$ and $C_L$/kg could change in any of several logical trajectories, a temporal indicator on the R-M plane can apprise a clinician of the patient's status.

Figure 5:
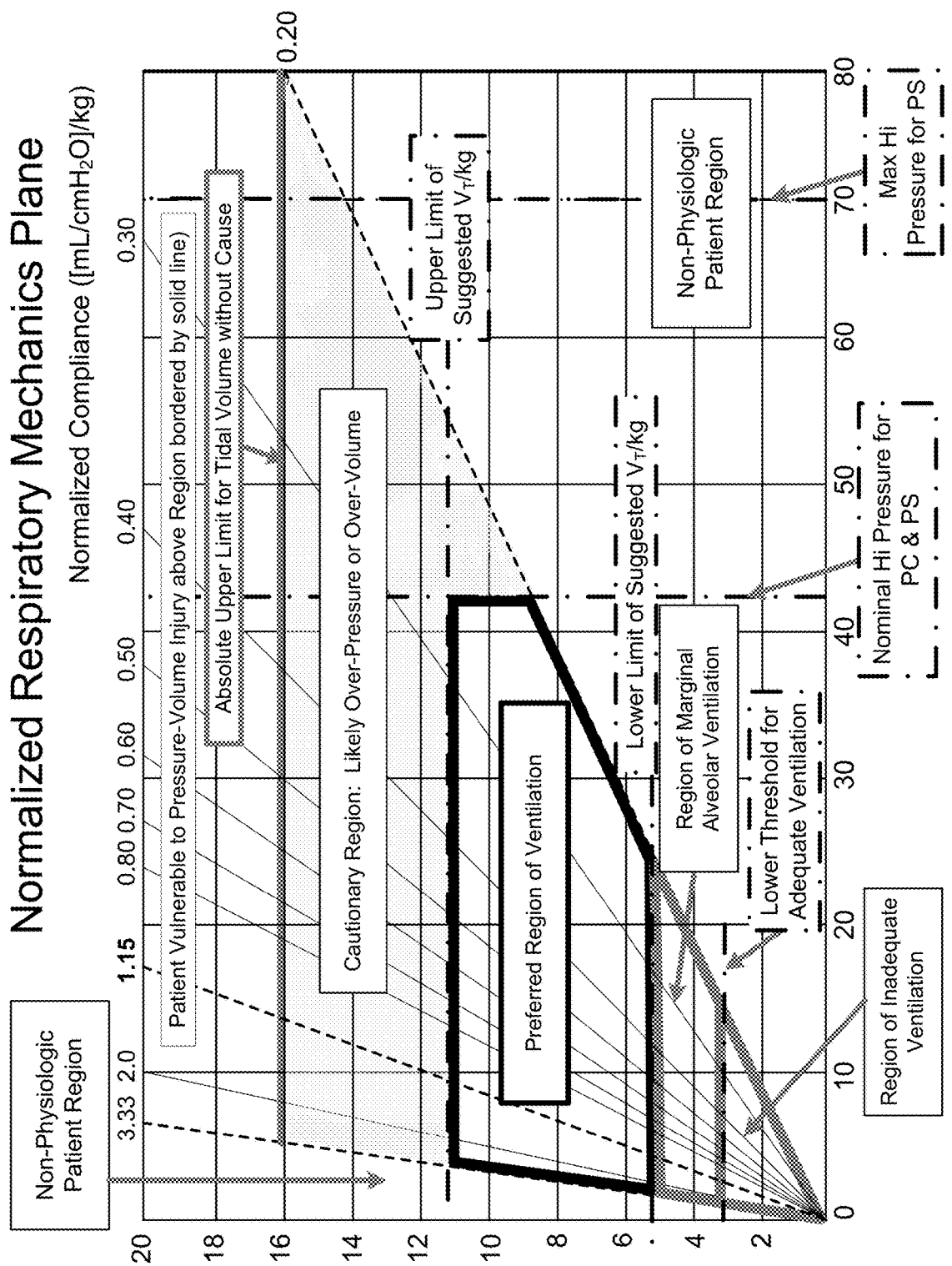
FIG. 5 is a chart illustrating an example of a normalized respiratory plane with provided boundaries in accordance with aspects of the disclosure.

FIG. 5 is a chart illustrating a normalized respiratory mechanics plane with provided boundaries. Similar to FIG. 3, FIG. 5 depicts the relationship between tidal volume (ml) and distending pressure ($\Delta P$ in $cmH_2O$) and provides boundaries that show better and worse ventilation areas on the chart. In some aspects, FIG. 5 could be displayed at each start-up on request. FIG. 5 reinforces in the clinician's mind the areas of better or worse ventilation. In some aspects, once the patient's PBW is known, the depiction of FIG. 5 is converted to the given patient or defaulted to the normalized patient as shown in FIG. 3.

In some embodiments, the ventilator system includes: means for ventilating a patient with the ventilator in a spontaneous breath subtype; means for non-invasively monitoring respiratory data of the patient with at least one of a pressure sensor and a flow sensor operatively coupled to at least one of a patient circuit or a pressure generating system; means for analyzing the respiratory data to detect a patient effort; means for delivering inspiratory gas to the patient with the ventilator in response to a detected patient effort; means for determining an occurrence of a condition by the ventilator based on information gathered by the ventilator; in response to the condition, means for determining a percent support setting for a PA breath subtype based on a target setting or the respiratory data from the spontaneous breath subtype; means for automatically and temporarily switching from the spontaneous breath subtype into the PA breath subtype for at least one breath in response to calculating the percent support setting; means for estimating a respiratory system compliance and/or respiratory system resistance of the patient during the PA breath subtype based on the respiratory data; means for returning to the spontaneous breath subtype after the at least three breaths; means for calculating a drive pressure of the patient during the spontaneous breath subtype utilizing the respiratory system compliance and/or the respiratory system resistance and the respiratory data; and means for performing an action based on the drive pressure. The spontaneous breath subtype does not include a proportional assist (PA) breath type.

Those skilled in the art will recognize that the methods and systems of the present disclosure may be implemented in many manners and as such are not to be limited by the foregoing exemplary embodiments and examples. In other words, functional elements being performed by a single or multiple components, in various combinations of hardware and software or firmware, and individual functions, can be distributed among software applications at either the client or server level or both. In this regard, any number of the features of the different embodiments described herein may be combined into single or multiple embodiments, and alternate embodiments having fewer than or more than all of the features herein described are possible. Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, and those variations and modifications that may be made to the hardware or software firmware components described herein as would be understood by those skilled in the art now and hereafter.

Numerous other changes may be made which will readily suggest themselves to those skilled in the art and which are encompassed in the spirit of the disclosure and as defined in the appended claims. While various embodiments have been described for purposes of this disclosure, various changes and modifications may be made which are well within the scope of the present invention. Numerous other changes may be made which will readily suggest themselves to those skilled in the art and which are encompassed in the spirit of the disclosure and as defined in the appended claims.

What is claimed is:

1. A method, performed by a ventilator, for ventilation of a patient with the ventilator, the method comprising:
    ventilating the patient with the ventilator in a spontaneous breath subtype, wherein the spontaneous breath subtype does not include a proportional assist (PA) breath subtype;
    non-invasively monitoring respiratory data of the patient with at least one of a pressure sensor and a flow sensor operatively coupled to at least one of a patient circuit or a pressure generating system;
    delivering inspiratory gas to the patient with the ventilator in response to a detected patient effort;
    determining a percent support setting for the PA breath subtype based on a target setting or the respiratory data monitored during the spontaneous breath subtype;
    automatically and temporarily switching from the spontaneous breath subtype into the PA breath subtype for at least three breaths, wherein the PA breath subtype is based on the percent support setting;
    estimating a respiratory system compliance and a respiratory system resistance of the patient, based on the respiratory data monitored during the PA breath subtype;
    returning to the spontaneous breath subtype after the at least three breaths;
    calculating a drive pressure of the patient based on:
        at least one of the respiratory system compliance or the respiratory system resistance, estimated during the PA breath subtype; and
        the respiratory data monitored after returning to the spontaneous breath subtype; and
    automatically performing an action by the ventilator, based on the drive pressure.

2. The method of claim 1, where the at least three breaths is from four to twelve breaths.

3. The method of claim 1, wherein a PEEP level for the PA breath subtype is set based on a PEEP level utilized in the spontaneous breath subtype.

4. The method of claim 1, wherein the action automatically performed by the ventilator includes changing the target setting.

5. The method of claim 1, wherein the action automatically performed by the ventilator includes providing a recommendation to a clinician based on the drive pressure.

6. The method of claim 1, further comprising displaying a normalized respiratory mechanics plane chart.

7. The method of claim 1, wherein the drive pressure is displayed in a graph versus time.

8. The method of claim 1, further comprising estimating a muscle pressure of the patient during the spontaneous breath subtype based on at least one of the respiratory system compliance or the respiratory system resistance.

9. The method of claim 1, further comprising determining an occurrence of a condition by the ventilator based on information gathered by the ventilator.

10. The method of claim 9, wherein the condition is a change of at least 25% in at least one of: monitored pressure, monitored tidal volume, or monitored flow.

11. The method of claim 9, wherein the condition is at least one of:
expiration of one hour from the last use of the PA breath subtype; or
a start of ventilation without a change of at least 25% in at least one of: monitored pressure, monitored tidal volume, or monitored flow.

12. The method of claim 1, wherein the action based on the drive pressure includes displaying the drive pressure.

13. The method of claim 12, wherein the action automatically performed by the ventilator includes adjusting ventilation parameters to maintain the drive pressure below 15 $cmH_2O$.

14. A ventilator system for delivering drive pressure ventilation to a patient, the ventilator system comprising:
a pressure generating system that generates a flow of breathing gas;
a ventilation tubing system including a patient interface for connecting the pressure generating system to the patient;
one or more non-invasive sensors operatively coupled to at least one of the pressure generating system or the ventilation tubing system, wherein the one or more non-invasive sensors generate output indicative of at least one of flow, volume or pressure;
a controller configured to cause the ventilator system to perform a set of operations including:
ventilating the patient with the ventilator in a spontaneous breath subtype, wherein the spontaneous breath subtype does not include a proportional assist (PA) breath subtype;
non-invasively monitoring respiratory data of the patient with the one or more non-invasive sensors;
delivering inspiratory gas to the patient with the ventilator in response to a detected patient effort;
determining a percent support setting for the PA breath subtype, based on a target setting or the respiratory data monitored during the spontaneous breath subtype;
automatically and temporarily switching from the spontaneous breath subtype into the PA breath subtype for at least three breaths, wherein the PA breath subtype is based on the percent support setting;
estimating a respiratory system compliance and a respiratory system resistance of the patient, based on the respiratory data monitored during the PA breath subtype;
returning to the spontaneous breath subtype after the at least three breaths;
calculating a drive pressure of the patient based on:
at least one of the respiratory system compliance or the respiratory system resistance, estimated during the PA breath subtype; and
the respiratory data monitored after returning to the spontaneous breath subtype; and
automatically performing an action by the ventilator, based on the drive pressure.

15. The ventilator system of claim 14, wherein a PEEP level for the PA breath subtype is set based on a PEEP level utilized in the spontaneous breath subtype.

16. The ventilator system of claim 14, wherein the operations further comprise determining an occurrence of a condition by the ventilator based on information gathered by the ventilator, and wherein the condition is a change of at least 25% in at least one of: monitored pressure, monitored tidal volume, or monitored flow.

17. The ventilator system of claim 14, wherein the operations further comprise determining an occurrence of a condition by the ventilator based on information gathered by the ventilator, and wherein the condition is expiration of 1 hour from the last use of the PA breath subtype or a start of ventilation without a change in monitored pressure, monitored tidal volume, or monitored flow of at least 25%.

18. The ventilator system of claim 14, wherein the action automatically performed by the ventilator, based on the drive pressure, includes changing the target setting.

19. The ventilator system of claim 14, wherein the action automatically performed by the ventilator, based on the drive pressure, includes adjusting ventilation parameters to maintain the drive pressure below 15 $cmH_2O$.

20. The ventilator system of claim 14, wherein the operations further comprise displaying a normalized respiratory mechanics plane chart.

* * * * *